United States Patent
Wang et al.

[11] Patent Number: 5,780,249
[45] Date of Patent: Jul. 14, 1998

[54] COMPETITIVE ASSAYS USING CHEMILUMINESCENT ELECTRON-RICH ARYL-SUBSTITUTED 1,2-DIOXETANES

[75] Inventors: Nai-Yi Wang, Mundelein; Roger C. Hu, Libertyville, both of Ill.

[73] Assignee: Abbott Laboratories, Abbott Park, Ill.

[21] Appl. No.: 437,343

[22] Filed: May 9, 1995

Related U.S. Application Data

[62] Division of Ser. No. 968,911, Oct. 30, 1992, Pat. No. 5,603,868.
[51] Int. Cl.⁶ .................. G01N 33/53; G01N 33/543
[52] U.S. Cl. .................. 435/7.93; 435/4; 435/6; 435/7.1; 435/7.9
[58] Field of Search .................. 435/4, 5, 6, 7.1, 435/7.9, 7.93; 549/215, 219, 220, 221

[56] References Cited

U.S. PATENT DOCUMENTS

| | | | |
|---|---|---|---|
| 4,931,569 | 6/1990 | Edwards et al. | 549/221 |
| 5,004,565 | 4/1991 | Schaap | 252/700 |
| 5,112,960 | 5/1992 | Bronstein et al. | 536/18.1 |

*Primary Examiner*—Ponnathapura Achutamurthy
*Attorney, Agent, or Firm*—Priscilla Porembski; John Levis; Regina Anderson

[57] ABSTRACT

Chemiluminescent electron-rich aryl-substituted 1,2-dioxetane compounds are disclosed in which the aryl group is poly-substituted with suitable electron-donating groups such that the light-emitting pattern of the molecule results in a very high luminescent count, thus providing for a sensitive and precise assay for haptens, analytes, polynucleotides and the like. These substituted aryl-containing 1,2-dioxetane compounds can be used as direct labels in an immunoassay or when derivatized with an appropriate leaving group, can be used as a substrate for a enzyme immunoassay. The unusual chemiluminescence of the compounds allows the timing of the luminescent reaction to be exactly controlled.

32 Claims, 3 Drawing Sheets

COMPETITIVE ASSAYS USING CHEMILUMINESCENT ELECTRON-RICH ARYL-SUBSTITUTED 1,2-DIOXETANES

This application is a Divisional of U.S. application Ser. No. 07/968,911 filed Oct. 30, 1992, now U.S. Pat. No. 5,603,868.

TECHNICAL FIELD

This invention relates to novel chemiluminescent dioxetane compounds. In particular, this invention relates to 1,2-dioxetane compounds containing an aryl group which is substituted with certain electron-rich substituents for use in assays.

BACKGROUND OF THE INVENTION

The utilization of chemiluminescent compounds, such as 1,2-dioxetanes in immunoassays, chemical assays, nucleic acid assays and other chemical/physical probe techniques is well known. See, for example, U.S. Pat. No. 4,931,223 to Bronstein et al. published Jun. 5, 1990; U.S. Pat. No. 4,931,569 to Brooks et al. published Jun. 5, 1990; U.S. Pat. No. 5,013,827 to Schaap, et al. published May 7, 1991; U.S. Pat. No. 5,068,339 to Schaap, et al. published Nov. 26, 1991, and U.S. Pat. No. 5,112,960 to Bronstein et al. published May 12, 1992.

It is known that the stability and chemiluminescence of dioxetanes can be altered by the attachment of specific substituents to the peroxide ring. See Zaklika et al. in *Photochem. Photobiol.*, 30, 35 (1979), Schaap et al, *J. Amer. Chem Soc.*, 104, 3504 (1982), and Handley et al., *Tetrahedron Lett.*, 3183 (1985). These authors have focused on various ways of substituting and stabilizing the spiro-fused polycyclic alkylene group as a way of improving the shelf-life at ambient temperatures of such compounds, as well as improving the chemiluminescent decomposition of the stabilized dioxetanes. In particular, the focus has been the adamantyl group spirofused to the 1,2-dioxetane. The compounds which have resulted suffer from the disadvantage of longer than optimal period of time needed to reach constant light emission. These compounds therefore are inadequate and suboptimal in assays where such a rapid release of light is critical, such as in a bioassay.

No examples of 1,2-dioxetane compounds are known that possess the critical property of rapid energy release in addition to providing for the kinetics of activation of the luminescer molecule to be exactly controlled according to need. Thus, it would be advantageous to provide such novel dioxetanes which provide for controllable, rapid release of light. Such compounds would be useful in immunoassays for various analytes and in probes using enzymes or other chemicals for triggering the dioxetanes to produce light from the luminescent portion of the molecule as a signal.

SUMMARY OF THE INVENTION

This invention provides a chemiluminescent compound of the Formula (I):

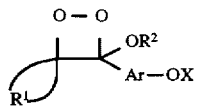

wherein Ar—OX represents an aryl group substituted with an X—oxy group. The aryl group is further substituted with one to four groups independently selected from the group consisting of $C_1$–$C_{10}$-alkyl, $C_1$–$C_{10}$-alkoxy, $C_1$–$C_{10}$-alkylthio, halo-$C_1$–$C_{10}$-alkyl, $C_1$–$C_{10}$-alkylamino, di-($C_1$–$C_{10}$-alkyl)amino, aryl-$C_1$–$C_{10}$-alkyl and halogen; OX is a chemically labile group wherein the removal of X by an activating agent results in the formation of an aryl oxide intermediate; $R^1$ is a polycyclic alkylene of from 6 to 30 carbon atoms having at least two fused rings, which is optionally substituted with up to ten groups independently selected from the group consisting of $C_1$–$C_{10}$-alkyl, $C_1$–$C_{10}$-alkoxy, halogen, and halo-$C_1$–$C_{10}$-alkyl; $R^2$ is independently selected from the group consisting of $C_1$–$C_{10}$-alkyl, halo-$C_1$–$C_{10}$-alkyl, $C_1$–$C_{10}$-arylalkyl, carboxy-$C_1$–$C_{10}$-alkyl, hydroxy-$C_1$–$C_{10}$-alkyl, aldehydo-$C_1$–$C_{10}$-alkyl, amino-$C_1$–$C_{10}$-alkyl, and thiol-$C_1$–$C_{10}$-alkyl. The chemiluminescence of Formula I is enzymatically or chemically induced to provide a rapid, controllable and sensitive luminescent count.

The present invention further provides an indicator reagent for use in assays, which indicator reagent comprises a chemiluminescent compound of the present invention attached to a specific binding member. The so-formed conjugate does not interfere with chemiluminescence measurement.

In one embodiment of the present invention, art-recognized assays that use the chemiluminescent dioxetane compounds of the present invention to test for the presence of an analyte which may be present in a test sample are provided. One such method comprises (a) contacting the test sample with an indicator reagent which specifically binds said analyte and is capable of generating a measurable signal, said indicator reagent comprising an analyte-specific binding member conjugated to a chemiluminescent compound of the present invention, and (b) detecting the signal generated from the indicator reagent as an indication of the presence of the analyte in the test sample.

In another embodiment, a method for determining the presence of an analyte which may be present in a test sample comprises (a) contacting the test sample with an enzyme conjugate which specifically binds said analyte, said enzyme conjugate comprising an enzyme conjugated to an analyte-specific binding member and adding an indicator reagent which is capable of generating a measurable signal and which comprises a dioxetane compound of the present invention, and (b) detecting the signal generated from the indicator reagent as an indication of the presence of the analyte in the test sample.

The present invention further provides for competitive assays for determining the presence and/or amount of analyte which may be present in a test sample. The method comprises (a) contacting the test sample suspected of containing the analyte with an analyte-specific binding member and an indicator reagent which is capable of generating a measurable signal comprising (i) said analyte or derivative of said analyte; and (ii) a chemiluminescent compound of the present invention for a time and under conditions sufficient to form indicator reagent/analyte-specific binding member and/or analyte/analyte-specific binding member complexes, and determining the presence of analyte present in the test sample by detecting the reduction in binding of the indicator reagent to the solid phase as compared to the signal generated from a negative test sample to indicate the presence of analyte in the test sample.

In yet another aspect, a competitive assay for determining the presence and/or amount of analyte which may be present in a test sample is provided. Such assay comprises (a) contacting the test sample suspected of containing the analyte with an analyte-specific binding member and an enzyme

3 conjugate comprising an enzyme and said analyte or derivative of said analyte and adding an indicator reagent capable of generating a measurable signal and which comprises a dioxetane compound of the present invention for a time and under conditions sufficient to form indicator reagent/ analyte-specific binding member-enzyme conjugate and/or analyte/analyte-specific binding member-enzyme conjugate complexes; and (b) determining the presence of analyte present in the test sample by detecting the reduction in binding of the indicator reagent as compared to the signal generated from a negative test sample to indicate the presence of analyte in the test sample.

In another embodiment of the invention, a competitive assay for determining the presence and amount of analyte which may be present in a test sample, comprises: (a) contacting the test sample suspected of containing the analyte with a solid phase to which an analyte-specific binding member has been attached and an indicator reagent capable of generating a measurable signal, said indicator reagent comprising (i) said analyte or analyte derivative and (ii) a dioxetane compound of the present invention for a time and under conditions sufficient to form a mixture of the test sample and solid phase and/or indicator reagent and solid phase; (b) determining the presence of analyte present in the test sample by detecting the reduction in binding of the indicator reagent to the solid phase as compared to the signal generated from a negative test sample to indicate the presence of analyte in the test sample The present invention also provides a test kit useful for detecting an analyte of interest in a test sample, the test kit comprising a container containing a chemiluminescent dioxetane compound of the present invention. The test kit further comprises a means for generating a detectable chemiluminescent signal, wherein said means is an enzyme or a chemical.

4

DETAILED DESCRIPTION

We have unexpectedly discovered that the substitution of electron-donating groups, substituted for hydrogen on the aryl group of a 1,2-dioxetane, drastically changes the light-emitting pattern of the dioxetane compounds of the present invention. Such a pattern is exemplified by detecting within 0.1 to 0.5 seconds a value of 17,000 counts (which accounts for more than 95% of the total light) from a test sample of $5 \times 10^{-18}$ moles of a compound of the present invention after triggering with 1M tetra-n-butylammonium fluoride in tetrahydrofuran (See FIG. 1A).

Figure 5:
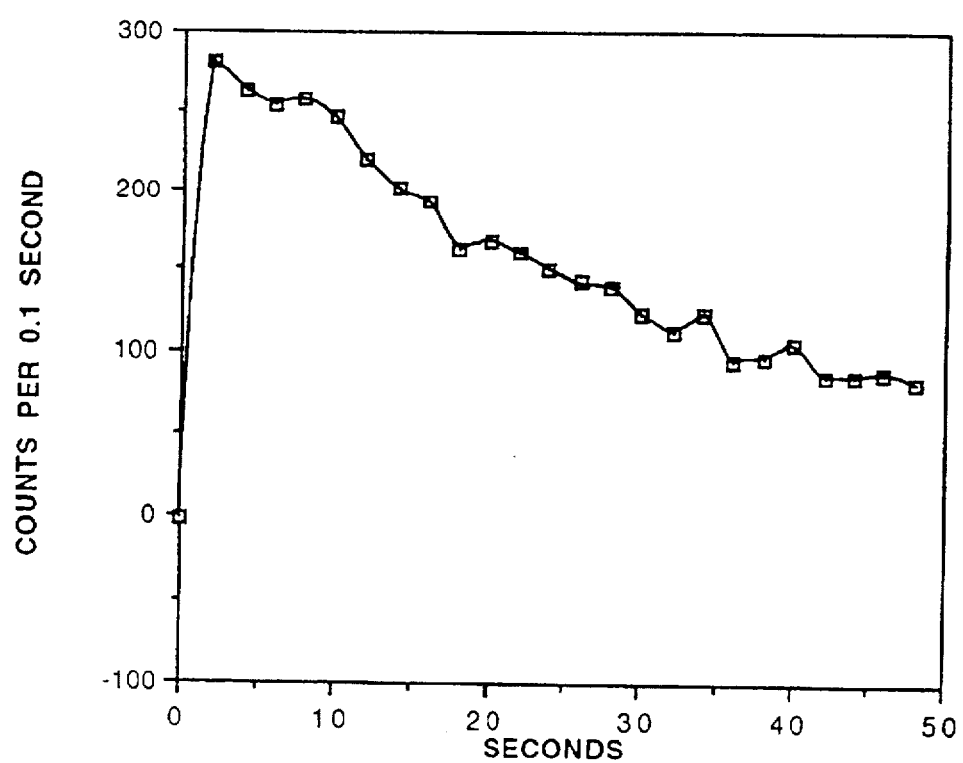
FIG. 5 is a graph showing the time profile of the chemical triggering of a control compound, 4-(3-tert-butyldimethylsilyloxyphenyl)-4-(4-hydroxybutyloxy) spiro{1,2-dioxetane-3,2'-(1',7',7'-trimethylbicyclo[2.2.1] heptane)} with tetra-n-butylammonium fluoride in THF.

The chemiluminescent profiles of exemplary electron-rich aryl-substituted dioxetanes of the present invention were compared to a control dioxetane compound comprising an unsubstituted aryl. The time course of luminescence for the known art compound 4-(3-tert-butyldimethylsilyloxyphenyl)-4-(4-hydroxybutyloxy) spiro{1,2-dioxetane-3,2'-(1',7',7'-trimethylbicyclo[2.2.1] heptane)} is shown in FIG. 5. The control demonstrates a broad emission curve, with emittance from 0 to 50 seconds. In contrast, the dioxetane compounds of the present invention have very short emission curves. Maximum luminescence of the compounds of the present invention in each case was approximately 0.5 seconds as illustrated in the Figures.

Very high luminescent counts that provide for sensitive and precise assays in which the timing of the luminescent reaction can be exactly controlled are obtained by utilizing the dioxetanes having the structure of the Formula (I):

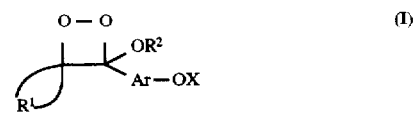

(I)

wherein Ar—OX represents an aryl group substituted with an X—oxy group. The aryl group is further substituted with one to four groups independently selected from the group consisting of $C_1$–$C_{10}$-alkyl, $C_1$–$C_{10}$-alkoxy, $C_1$–$C_{10}$-alkylthio, halo-$C_1$–$C_{10}$-alkyl, $C_1$–$C_{10}$-alkylamino, di-($C_1$–$C_{10}$-alkyl)amino, aryl-$C_1$–$C_{10}$-alkyl and halogen; OX is a chemically labile group wherein the removal of X by an activating agent results in the formation of an aryl oxide intermediate;

$R^1$ is a polycyclic alkylene of from 6 to 30 carbon atoms having at least two fused rings, which is optionally substituted with up to ten groups independently selected from the group consisting of $C_1$–$C_{10}$-alkyl, $C_1$–$C_{10}$-alkoxy, halogen, and halo-$C_1$–$C_{10}$-alkyl; $R^2$ is independently selected from the group consisting of $C_1$–$C_{10}$-alkyl, halo-$C_1$–$C_{10}$-alkyl, $C_1$–$C_{10}$-arylalkyl, carboxy-$C_1$–$C_{10}$-alkyl, hydroxy-$C_1$–$C_{10}$-alkyl, aldehydo-$C_1$–$C_{10}$-alkyl, amino-$C_1$–$C_{10}$-alkyl, and thiol-$C_1$–$C_{10}$-alkyl.

More preferably, the dioxetane compounds of the present invention have the structure of Formula (II):

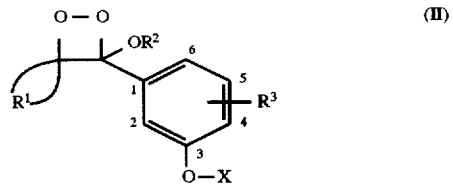

(II)

wherein $R^1$, $R^2$, and X are as defined above and $R^3$ is up to four groups selected from $C_1$–$C_{10}$-alkyl, $C_1$–$C_{10}$-alkoxy, $C_1$–$C_{10}$-alkylthio, halo-$C_1$–$C_{10}$-alkyl, $C_1$–$C_{10}$-alkylamino, $C_1$–$C_{10}$-dialkylamino and aryl-$C_1$–$C_{10}$-alkyl.

In a more preferred embodiment, $R^1$ of Formula II is substituted or unsubstituted adamantyl or bicyclo [2.2.1] heptyl, and $R^3$ is at position 4 and is $C_1$–$C_{10}$-alkyl or $C_1$–$C_{10}$-alkoxy. In a most preferred embodiment, $R^3$ is methyl or methoxy.

Another preferred embodiment of the present invention is represented by the compound of Formula (III):

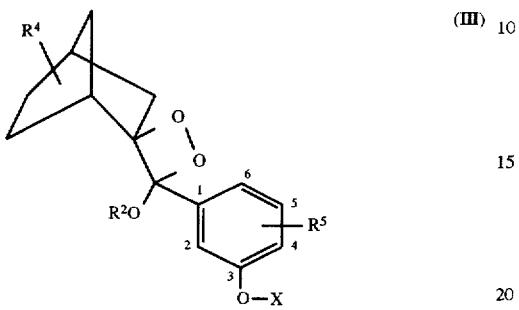

(III)

wherein $R^4$ is from zero to nine groups independently selected from the group consisting of hydrogen, $C_1$–$C_{10}$-alkyl, $C_1$–$C_{10}$-alkoxy, halo-$C_1$–$C_{10}$-alkyl and halogen, $R^5$ is hydrogen, $C_1$–$C_{10}$-alkyl or $C_1$–$C_{10}$-alkoxy and $R^4$, $R^2$ and OX are as defined. In a more preferred embodiment, $R^5$ is at position 4 and is methyl or methoxy.

Yet another preferred embodiment of the present invention is represented by Formula (IV):

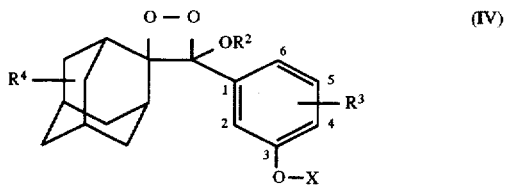

(IV)

More preferably, $R^3$ of Formula IV is $C_1$–$C_{10}$-alkyl or $C_1$–$C_{10}$-alkoxy; $R^2$ is methyl, —(CH$_2$)$_n$OH or —(CH$_2$)$_n$CHO, wherein n is from one to nine; and $R^4$ and OX are as defined. Most preferably, $R^3$ is at position 4 and is methyl or methoxy.

Another preferred embodiment of the present invention is represented by Formula (V):

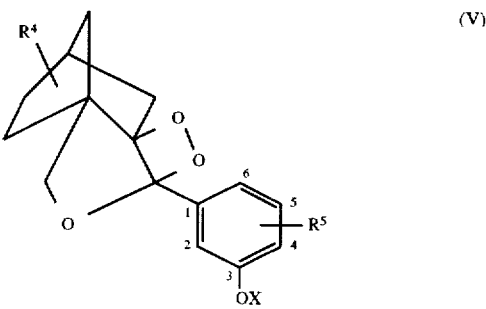

(V)

wherein $R^5$ is hydrogen, $C_1$–$C_{10}$-alkyl or $C_1$–$C_{10}$-alkoxy, and $R^4$ and X are as defined. Most preferably, $R^5$ is at position 4 and is methyl or methoxy.

In general, the adamantane- or norbornane-containing dioxetanes of the present invention are synthesized as shown in Schemes I and II below.

Referring to Scheme I, the phenolic group of 3-hydroxybenzoic acid which may be substituted with up to four electron-donating groups is selectively protected, preferably, but not exclusively, as the tert-butyldimethylsilylether. Esterification of the free acid with an alcohol ($R^2$OH) gives the corresponding ester which, after coupling to an optionally substituted bicyclic ketone such as camphor or a tricyclic ketone such as adamantanone, is photooxygenated as described in U.S. Pat. No. 5,013,827 to produce the desired 1,2-dioxetane.

Alternatively, the protecting group in the enol ether can be removed and the liberated phenolic group phosphorylated as described in U.S. Pat. No. 5,013,827. Photooxygenation of the enol-phosphate affords the dioxetane which can be triggered by enzymes such as alkaline phosphatase and the like. Scheme I illustrates the coupling of the camphor moiety with the enol ether. It is within the scope of the present invention that analogous conditions would apply for the coupling with adamantanone.

The general method for synthesizing the bridged dioxetane compound is illustrated in Scheme II. Referring to Scheme II, when the alcohol group is built in the polycyclic moiety, such as the bicyclic system shown, the coupling becomes intramolecular, and the reaction gives a cyclic enol ether. Photooxygenation of the coupled compound produces the chemical-cleavable or enzyme-cleavable dioxetane as shown in Scheme II.

Scheme I

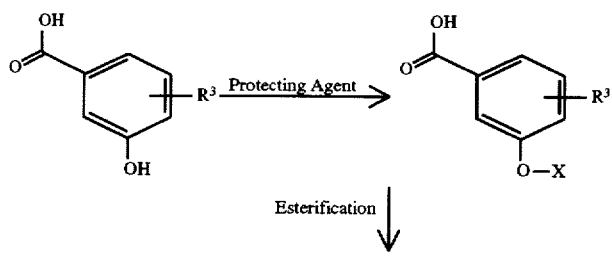

Esterification

-continued
Scheme I
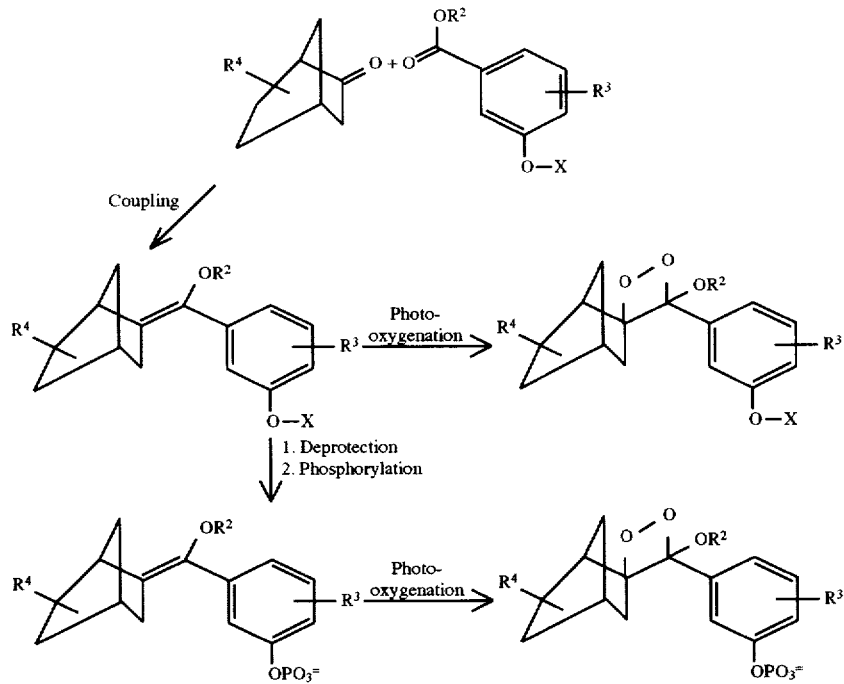
Scheme II
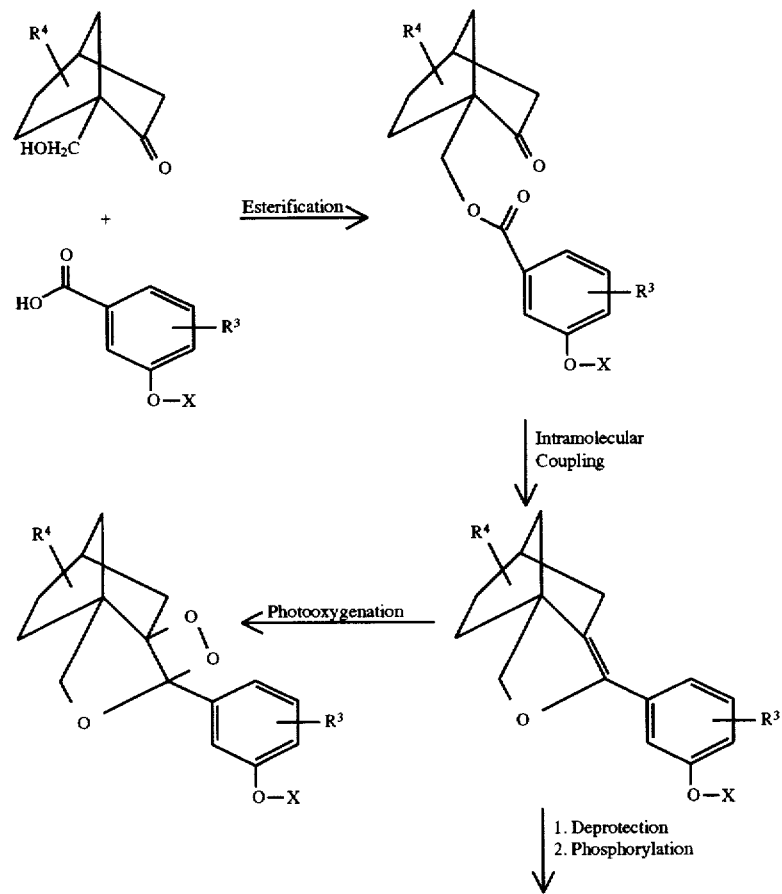

-continued
Scheme II

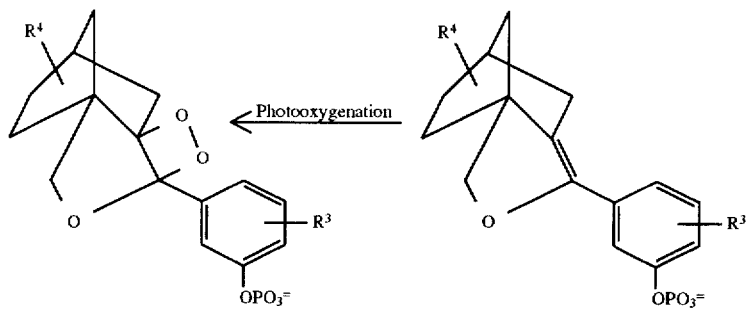

DEFINITIONS

As used herein, the following terms shall have the following meanings:

"Aryl substituted by OX" is phenyl, biphenyl, 9,10-dihydrophenanthryl, naphthyl, anthryl, pyridyl, quinolinyl, isoquinolinyl, phenanthryl, pyrenyl, coumarinrinyl, carbostyrl, acridinyl, phthalyl or derivatives thereof, substituted with an OX group removable by an activating agent to form an unstable 1,2-dioxetane derivative which decomposes to generate light energy.

"$C_1$–$C_{10}$-alkyl" refers to saturated or unsaturated, branched or straight chain alkyl groups having 1 to 10 carbon atoms, e.g., methyl, n-butyl or decyl.

"$C_1$–$C_{10}$-alkoxy" refers to an alkoxy group in which the alkyl portion is saturated or unsaturated, branched or straight chain of 1 to 10 carbon atoms, e.g., methoxy or ethoxy.

"Halo-$C_1$–$C_{10}$-alkyl" refers to a haloalkyl group in which the alkyl portion is a saturated or unsaturated, branched or straight chain of from 1 to 10 carbon atoms, e.g., iodomethyl.

"Hydroxy-$C_1$–$C_{10}$-alkyl" refers to hydroxyalkyl group, in which the alkyl portion is branched or straight chain, saturated or unsaturated of 1 to 10 carbon atoms, e.g., hydroxymethyl or hydroxyethyl.

"Aldehydo-$C_1$–$C_{10}$-alkyl" refers to an aldehydo group, in which the alkyl portion is a saturated or unsaturated, branched or straight chain of 1 to 10 carbon atoms, e.g., hydroxymethyl or hydroxyethyl.

"Polycyclic alkylene of from 6 to 30 carbon atoms" refers to a stability-providing, fused or unfused cycloalkyl, cycloalkylidene or polycycloalkylidene group bonded to the 3-carbon of the dioxetane ring carbon atoms, inclusive of, adamantane, camphorane, norbornane, pentalene, and the like, as well as derivatives thereof. The fused polycyclic ring portion of the fluorophore moiety represented by $R^1$ also can be the residue of a fused polycyclic aromatic or nonaromatic heterocyclic ring fluorophoric compound, such as, benzo[b]thiophene, naphtho[2,3-b]thiophene, thianthrene, benzofuran, isobenzofuran, chromene, xanthene, phenoxathin, quinoline, isoquinoline, phenanthridine, phenazine, phenoxazine, phenothiazine, phenanthroline, purine, 4H-quinolizine, phthalazine, naphthyridine, indole, indolizine, chroman, isochroman, indoline, isoindoline, and the like, unsubstituted or substituted, with one or more of the aforementioned non-labile substituents.

"Chemically labile group" is a group capable of forming an anion upon enzymatic or chemical cleavage. Chemically labile groups include but are not limited to hydroxyl, alkyl or aryl ester, inorganic oxyacid salt, alkyl or aryl silyloxy and oxygen-pyranoside.

"Indicator reagent" is a conjugate formed by coupling a chemiluminescent dioxetane compound of the present invention to a specific binding member, as defined below. The coupling may occur through an amine, an aldehyde, a sulfhydryl, a maleimide, a carboxylic acid group, a hydroxyl group, and the like.

"Enzyme conjugate" is a conjugate formed by coupling an enzyme to specific binding member as defined below or to an analyte or derivative of that analyte. The coupling may occur through an amide, ester, thioether, Schiff base, substituted amine, disulfide, and the like "Specific binding member," is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding member, for example, an analyte-analog. Immunoreactive specific binding members include antigens, antigen fragments; antibodies and antibody fragments, both monoclonal and polyclonal; and complexes thereof, including those formed by recombinant DNA methods. Antigen and antigen fragments include any which can be derived or produced and are useful in assays, including viral and native lysates, synthetic peptides, recombinant proteins and the like.

"Polynucleotide" is a polymer of many nucleotides, e.g., RNA and DNA.

"Analyte," is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. As a member of a specific binding pair, the analyte can be detected by means of naturally occurring specific binding partner (pairs) such as the use of intrinsic factor protein as a member of a specific binding pair for the determination of Vitamin B12 or the use of lectin as a member of a specific binding pair for the determination of a carbohydrate. The analyte can include a protein, peptide, an amino acid, a hormone, a steroid, a vitamin, a drug including those administered for therapeutic purposes as well as those administered for illicit purpose, a bacterium, a virus, and metabolites or or antibodies to the above substances.

"Analyte-specific binding member" refers to a member such as an antibody or receptor that specifically binds to the analyte. It commonly refers to a group consiting of an antigen, an antibody, a hapten, a polynucleotide, carbohydrate, and a small molecular weight analyte.

"Hapten" refers to a partial antigen or non-protein binding member which is capable of binding to an antibody, but which is not capable of eliciting antibody formation unless coupled to a carrier protein.

"Solid phase" refers to any material which is insoluble, or can be made insoluble by a subsequent reaction.

"Capture reagent" refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

GENERAL DESCRIPTION OF ASSAYS

The chemiluminescent, aryl-substituted 1,2-dioxetane compounds of the present invention are useful in assays, including assays for detecting analytes in test samples, as constituents in test kits useful in such assays, and for like uses and means for accomplishing such uses.

In general, art-recognized assays using the dioxetane compounds of the present invention can be performed as follows. A test sample suspected of containing an analyte is contacted with a buffered solution containing an enzyme bonded to a specific binding member for the analyte to form a mixture. This mixture is incubated for a time and under conditions to allow the analyte to bind to the analyte-specific binding member-enzyme compound, thus forming analyte/ analyte-specific binding member-enzyme complexes. After washing a dioxetane having a group cleavable by the enzyme portion of the analyte-specific binding member-enzyme compound is added to the mixture. The enzyme cleaves the enzyme-cleavable group, causing the dioxetane to decompose into two carbonyl compounds (e.g., an ester, a ketone or an aldehyde). The chromophore to which the enzyme-cleavable group had been bonded thus is excited and luminesces. Luminescence is detected (using, e.g., a cuvette, or light-sensitive film in a camera luminometer, or a photoelectric cell or photomultiplier tube), as an indication of the presence of the analyte in the test sample. Luminescence intensity is measured to determine the concentration of the analyte.

The assay preferably is performed as an immunoassay, although the present invention is not limited to immunoreactive assays. Any assay utilizing specific binding members can be performed. As a member of a specific binding pair, the analyte, as defined above, can be detected by means of naturally occurring specific binding partners (pairs) such as the use of intrinsic factor protein in the capture and/or indicator reagents for the determination of vitamin $B_{12}$, or the use of a lectin in the capture and/or indicator reagents for the determination of a carbohydrate.

The analyte can include a hapten, polynucleotide, small molecular weight analyte, a protein, a peptide, an amino acid, a hormone, a steroid, a vitamin, a drug including those administered for therapeutic purposes as well as those administered for illicit purposes, a bacterium, a virus, and metabolites of or antibodies to any of the above substances.

The test sample can be a mammalian biological fluid such as whole blood or whole blood components including red blood cells, white blood cells including lymphocyte or lymphocyte subset preparations, platelets, serum and plasma; ascites; saliva; stools; cerebrospinal fluid; urine; sputum; trachael aspirates and other constituents of the body which may contain or be suspected of containing the analyte (s) of interest. The test sample also can be a culture fluid supernatant, or a suspension of cultured cells. Mammals whose body fluids can be assayed for an antigen analyte or an antibody analyte according to the present invention include humans and primates, as well as other mammals who are suspected of containing these analytes of interest. It also is contemplated that non-mammalian biological fluid test samples and non-biological fluid test samples can be utilized.

The indicator reagent comprises a specific binding member of the analyte conjugated to the label which is a chemiluminescent dioxetane of the present invention. The indicator reagent produces a detectable signal at a level relative to the amount of the analyte in the test sample. It is contemplated and within the scope of the present invention that more than one analyte can be assayed simultaneously. For example, the indicator reagent, while comprising a specific binding member of a different analyte, can be conjugated to the same signal generating dioxetane compound, which is capable of generating a detectable signal. In general, the indicator reagent is detected or measured after it is captured on the solid phase material. In the present invention, the total signal generated by the indicator reagent(s) indicates the presence of one or more of the analytes in the test sample. It is contemplated that any of the chemiluminescent dioxetane compounds of the present invention can be utilized as signal generating compounds. The preferred labels include:

4-(3-tert-butyldimethylsilyloxy-4-methoxyphenyl)-4-methoxyspiro[1,2-dioxetane-3,2'-adamantane] corresponding to

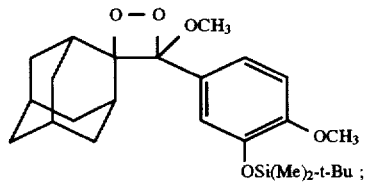

4-(3-phosphate-4-methoxyphenyl)-4-methoxyspiro[1,2-dioxetane-3,2'-adamantane], tetra-ethylammonium salt, corresponding to

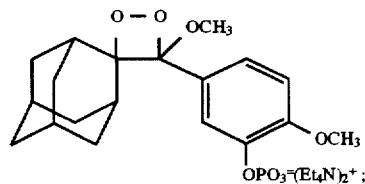

4-(3-tert-butyldimethylsilyloxy-4-methoxyphenyl)-4-methoxyspiro {1,2-dioxetane-3,2'-(1',7',7'-trimethylbicyclo [2.2.1]heptane)} corresponding to

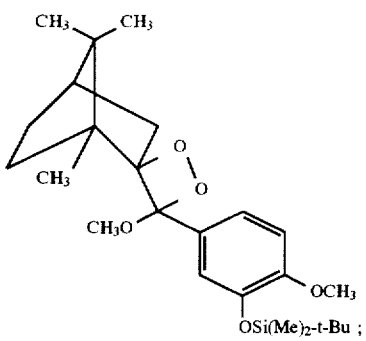

4-(3-tert-butyldimethylsilyloxy-4-methoxyphenyl)-4-(4-hydroxybutyloxy)spiro{1,2-dioxetane-3,2'-(1',7',7'-trimethyl bicyclo [2.2.1]heptane)} corresponding to

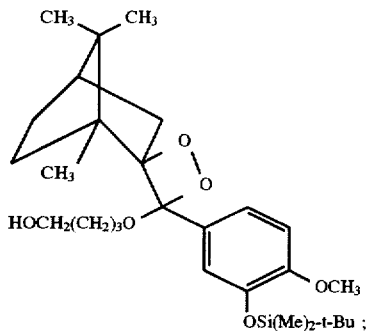

4-(3-tert-butyldimethylsilyloxy-4-methoxyphenyl)-4(-hydroxybutyl)oxyspiro[1,2-dioxetane-3,2'-adamantane] corresponding to

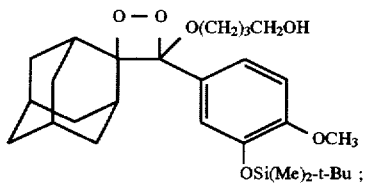

4-(3-tert-butyldimethylsilyloxy-4-methoxy)phenylspiro){4,1'-(epoxymethano)-1,2-dioxetane-3,2'-(7',7'-dimethylbicyclo[2.2.1]heptane)} corresponding to

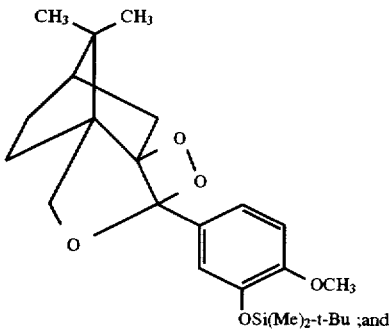

4-(3-tert-butyldimethylsilyloxy-4-methylphenyl)-4-methoxyspiro{1,2-dioxetane-3,2'-(1',7',7'-trimethyl bicyclo [2.2.1]heptane)} corresponding to

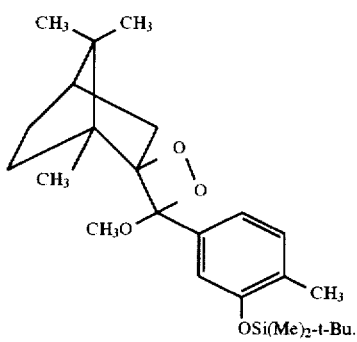

It is also contemplated that different luminescent compounds can be utilized as the signal generating compounds, one for each indicator reagent, and detection then could be determined by reading at different wavelengths or at different times. For example, a dioxetane compound of the present invention can be used in combination with a slower acting label known in the art, such as those described in U.S. Pat. No. 5,112,960 and U.S. Pat. No. 4,931,223. Methods which detail the use of two or more chemiluminescent compounds which are capable of generating signals at different times are the subject matter of co-pending patent application U.S. Ser. No. 636,038, abandoned, which enjoys common ownership and is incorporated herein by reference.

A wide variety of other assays exist which use visually detectable means to determine the presence or concentration of a particular substance in a test sample. The above-described dioxetanes can be used in any of these assays. Examples of such assays include immunoassays to detect antibodies or antigens, e.g., β-hCG; enzyme assays, chemical assays to detect, e.g., potassium or sodium ions; and nucleic acid assays to detect, e.g., viruses (e.g., HIV-I or cytomegalovirus), bacteria (e.g., *E. coli*), and certain cell functions (e.g., receptor binding sites).

In addition to being either an antigen or an antibody member of a specific binding pair, the specific binding member of the indicator reagent can be a member of any specific binding pair, including either biotin or avidin, a carbohydrate or a lectin, a complementary nucleotide sequence, an effector or a receptor molecule, an enzyme cofactor or an enzyme, an enzyme inhibitor or an enzyme, and the like. An immunoreactive specific binding member can be an antibody, an antigen, or an antibody/antigen complex that is capable of binding either to the analyte as in a sandwich assay, to the capture reagent as in a competitive assay, or to the ancillary specific binding member as in an indirect assay. If an antibody is used, it can be a monoclonal antibody, a polyclonal antibody, an antibody fragment, a recombinant antibody, a mixture thereof, or a mixture of an antibody and other specific binding members. The details of the preparation of such antibodies and their suitability for use as specific binding members are well known to those in the art.

The capture reagents of the present invention comprise a specific binding member for each of the analytes of interest which are attached to at least one solid phase and which are unlabeled. Although the capture reagent is specific for the analyte as in a sandwich assay, it can be specific for indicator reagent or analyte in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample. This attachment can be achieved, for example, by coating the specific binding member onto the solid phases by absorption or covalent coupling. Coating methods, and other known means of attachment, are known to those in the art.

The specific binding member of the capture reagent can be any molecule capable of specifically binding with another molecule. The specific binding member of the capture reagent can be an immunoreactive compound such as an antibody, antigen, or antibody/antigen complex. If an antibody is used, it can be a monoclonal antibody, a polyclonal antibody, an antibody fragment, a recombinant antibody, a mixture thereof, or a mixture of an antibody and other specific binding members.

The solid phase is not critical and can be selected by one skilled in the art. Thus, latex particles, microparticles, magnetic or non-magnetic beads, membranes, plastic tubes, walls of wells of reaction trays, glass or silicon chips and tanned sheep red blood cells are all suitable examples. Suitable methods for immobilizing capture reagents on solid phases include ionic, hydrophobic, covalent interactions and the like. Further, combinations of solid phases are contemplated and within the scope of the invention as exemplified by co-pending U.S. Ser. No. 07/574,821 filed Aug. 29, 1990, abandoned, which enjoys common ownership and is incorporated herein by reference. It is contemplated that if combinations of solid phases are utilized in an assay, then all solid phases be present during the quantitation of signal, thus eliminating the need to separate solid phases for detection of signal.

The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. Such useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents including monoclonal antibodies. Nylon also possesses similar characteristics and also is suitable.

It is contemplated that such porous solid supports described herein above are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces.

Preferred solid phase materials for flow-through assay devices include filter paper such as a porous fiberglass material or other fiber matrix materials. The thickness of such material is not critical and will be a matter of choice, largely based upon the properties of the test sample or analyte being assayed, such as the fluidity of the test sample.

To change or enhance the intrinsic charge of the solid phase, a charged substance can be coated directly to the material or onto microparticles which then are retained by a solid phase support material. Alternatively, microparticles can serve as the solid phase, by being retained in a column or being suspended in the mixture of soluble reagents and test sample, or the particles themselves can be retained and immobilized by a solid phase support material. By "retained and immobilized" is meant that the particles on or in the support material are not capable of substantial movement to positions elsewhere within the support material. The particles can be selected by one skilled in the art from any suitable type of particulate material and include those composed of polystyrene, polymethylacrylate, polypropylene, latex, polytetrafluoroethylene, polyacrylonitrile, polycarbonate, or similar materials. The size of the particles is not critical, although it is preferred that the average diameter of the particles be smaller than the average pore size of the support material being used. Thus, embodiments which utilize various other solid phases also are contemplated and are within the scope of this invention. For example, ion capture procedures for immobilizing an immobilizable reaction complex with a negatively charged polymer, described in co-pending U.S. patent application Ser. No. 150,278, abandoned, corresponding to EP Publication No. 0326100, and U.S. patent application Ser. No. 375,029, abandoned, (EP Publication No. 0406473), which enjoy common ownership and are incorporated herein by reference, can be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using various signal generating systems previously described, including those described in chemiluminescent signal measurements as described in co-pending U.S. patent application Ser. No. 921,979, abandoned, corresponding to EPO Publication No. 0273,115, which enjoys common ownership and which is incorporated herein by reference.

The present invention provides homogeneous and heterogenous assays which utilize the novel compounds described herein. While many assays described herein utilize solid phases, solid phases are not required to perform many of these assays. Also provided are direct, sandwich and competitive assays. For example, art-recognized assays that use the chemiluminescent dioxetane compounds of the present invention to test for the presence of an analyte which may be present in a test sample are provided. One such method comprises (a) contacting the test sample with an indicator reagent which specifically binds said analyte and is capable of generating a measurable signal, said indicator reagent comprising an analyte-specific binding member conjugated to a chemiluminescent compound of the present invention, and (b) detecting the signal generated from the indicator reagent as an indication of the presence of the analyte in the test sample.

Another method for determining the presence of an analyte which may be present in a test sample comprises(a) contacting the test sample with an enzyme conjugate which specifically binds said analyte, said enzyme conjugate comprising an enzyme conjugated to an analyte-specific binding member; adding an indicator reagent which is capable of generating a measurable signal and which comprises a dioxetane compound of the present invention, and (b) detecting the signal generated from the indicator reagent as an indication of the presence of the analyte in the test sample.

Competitive assays for determining the presence and/or amount of analyte which may be present in a test sample are also contemplated to be within the scope of the invention. Such a method comprises (a) contacting the test sample suspected of containing the analyte with an analyte-specific binding member and an indicator reagent which is capable of generating a measurable signal comprising (i) said analyte or derivative of said analyte; and (ii) a chemiluminescent compound of the present invention and determining the presence of analyte present in the test sample by detecting the reduction in binding of the indicator reagent to the solid phase as compared to the signal generated from a negative test sample to indicate the presence of analyte in the test sample.

In another embodiment, a competitive assay for determining the presence and/or amount of analyte which may be present in a test sample is provided. Such assay comprises (a) contacting the test sample suspected of containing the analyte with an analyte-specific binding member and an enzyme conjugate comprising an enzyme and said analyte or derivative of said analyte and adding an indicator reagent capable of generating a measurable signal and which comprises a dioxetane compound of the present invention for a time and under conditions sufficient to form indicator reagent/analyte-specific binding member-enzyme conjugate and/or analyte/analyte-specific binding member-enzyme conjugate complexes; and (c)determining the presence of analyte present in the test sample by detecting the reduction in binding of the indicator reagent as compared to the signal generated from a negative test sample to indicate the presence of analyte in the test sample.

In yet another embodiment of the invention, a competitive assay for determining the presence and amount of analyte which may be present in a test sample, comprises: (a)contacting the test sample suspected of containing the analyte with a solid phase to which an analyte-specific binding member has been attached and an indicator reagent capable of generating a measurable signal, said indicator reagent comprising (i) said analyte or analyte derivative and (ii) a dioxetane compound of the present invention for a time and under conditions sufficient to form a mixture of the test sample and solid phase and/or indicator reagent and solid phase; (b) determining the presence of analyte present in the test sample by detecting the reduction in binding of the indicator reagent to the solid phase as compared to the signal generated from a negative test sample to indicate the presence of analyte in the test sample The present invention also provides a test kit useful for detecting an analyte of interest in a test sample, the test kit comprising a container containing a chemiluminescent dioxetane compound of the present invention. The test kit further comprises a means for generating a detectable chemiluminescent signal, wherein said means is an enzyme or a chemical.

Also, the methods of the present invention can be adapted for use in systems which utilize microparticle technology including automated and semi-automated systems wherein the solid phase comprises a microparticle. Such systems include those described in pending U.S. patent application Ser. No. 425,651, now U.S. Pat. No. 5,244,630 and U.S. Pat. No. 5,089,424, which correspond to published EPO applications Nos. EP 0 425 633 and EP 0 424 634, respectively, and U.S. Pat. No. 5,006,309 all of which enjoy common ownership and are incorporated herein by reference. Further different analytes may be tested when using microparticles as solid phases. For example, more than one analyte may be attached to each microparticle. Or, one analyte may be attached to one microparticle and more than one analyte may be detected by combining microparticles having different analytes individually attached to form a mixture or "cocktail" of microparticles utilizable in any assay.

Further assay formats of the present invention are contemplated. For example, a test sample suspected of containing an analyte is contacted with a solid phase to which an analyte-specific binding member of the analyte is attached. The specific binding member serve as a capture reagent to bind the analyte to the solid phase. If the specific binding member is an immunoreactant, it can be an antibody, antigen, or complex thereof. This mixture is incubated for a time and under conditions sufficient for a binding reaction to occur and which incubation results in the formation of capture reagent/analyte complexes of the analyte if it is present in the test sample. Then, an indicator reagent for the analyte is contacted with the complexes. The indicator reagent for the analyte comprises a specific binding member of the analyte of interest which has been labeled with a signal generating dioxetane compound of the present invention. This mixture is incubated for a time and under conditions sufficient to form capture reagent/first analyte/indicator reagent complexes. The presence of the analyte is determined by detecting the signal generated in connection with the complexes formed on the solid phase as an indication of the presence of the analyte in the test sample. The label can be detected by the measurement of chemiluminescence on the label used to generate the signal.

In another assay format a test sample suspected of containing an analyte of interest is simultaneously contacted with a solid phase to which an analyte-specific binding member of a first analyte is attached, and a solid phase to which a first specific binding member of a second analyte has been attached, thereby forming a mixture. The specific binding members serve as capture reagents to bind the analyte(s) to the solid phases. If the specific binding member is an immunoreactant, it can be an antibody, antigen, or complex thereof, specific for each analyte of interest. If the specific binding member is an antibody, it can be a monoclonal or polyclonal antibody, an antibody fragment, a recombinant antibody, as well as a mixture thereof, or a mixture of an antibody and other specific binding members. This mixture is incubated for a time and under conditions sufficient for a binding reaction to occur and which incubation results in the formation of capture reagent/first analyte complexes of the first analyte if it is present in the test sample, and/or the formation of capture reagent/second analyte complexes of the second analyte if it is present in the test sample. Then, an indicator reagent for each analyte is contacted with the complexes. The indicator reagent for the first analyte comprises a specific binding member of the first analyte of interest which has been labeled with a signal generating dioxetane compound of the present invention. The indicator reagent for the second analyte comprises a specific binding member of the second analyte of interest which has been labeled with the same signal generating compound as the indicator reagent for the first analyte, thereby forming a second mixture. This second mixture is incubated for a time and under conditions sufficient to form capture reagent/first analyte/indicator reagent complexes and/or capture reagent/second analyte/indicator reagent complexes. The presence of either analyte is determined by detecting the signal generated in connection with the complexes formed on the solid phase as an indication of the presence of one or more analytes in the test sample. The label can be detected by the measurement of chemiluminescence on the label used to generate the signal.

The capture reagents can be attached to the same solid phase, or can be attached to different solid phases. It is contemplated that all capture reagents could be attached to the same solid phase, or that each capture reagent could be attached to a separate solid phase, or that combination of capture reagents could be attached to separate solid phases. For example, if microparticles were the solid phase of choice, then separate microparticles could have at least one capture reagent(s) attached to it. A mixture of microparticles (solid phases) could be used to capture the various analytes which may be present in the test sample by using the mixture of microparticles. It is contemplated that different ratios of capture reagents attached to solid phases could be utilized in such an assay, to optimize analyte(s) detection.

In yet another example of an assay format, a test sample suspected of containing any of the analytes of interest is simultaneously contacted with a first solid phase to which a first specific binding member of a first analyte and a first specific binding member of a second analyte have been attached, an indicator reagent for the first analyte comprising a specific binding member for the first analyte labeled with a signal generating compound and an indicator reagent for the second analyte comprising a specific binding member for the second analyte labeled with a signal generating compound, to form a mixture. The specific binding members serve as capture reagents to bind the analyte(s) to the solid phases. If the specific binding member is an immunoreactant, it can be an antibody, antigen, or complex thereof, specific for each analyte of interest. If the specific binding member is an antibody, it can be a monoclonal or polyclonal antibody, an antibody fragment, a recombinant antibody, as well as a mixture thereof, or a mixture of an antibody and other specific binding members. The indicator reagents comprise specific binding members of the first and second analytes of interest which have been labeled with a signal generating compound. This mixture is incubated for a time and under conditions sufficient for a binding reaction to occur and which incubation results in the formation of capture reagent/first analyte/indicator reagent complexes of the first analyte and/or capture reagent/second analyte/indicator reagent complexes of the second analyte, if either or both the first or second analyte are present in the test sample. The presence of either analyte is determined by detecting the signal generated in connection with the complexes formed on either or both solid phases as an indication of the presence of the first analyte and/or the second analyte in the test sample. If the indicator employs an enzyme as the signal generating compound (label), then the signal can be detected visually or measured spectrophotometrically with a luminometer. Luminometers are commercially available from MGM Instruments, Inc. Hamden, Conn. 06415 and other sources. Also, it is contemplated that the assay can include the use of a hapten-anti-hapten system, in which case the indicator reagent can further comprise a hapten such as biotin. The use of a biotin/anti-biotin system for assays is the subject matter of co-pending U.S. patent application Ser. No. 687,785 which corresponds to published European Patent Application No. 0160900 (published Nov. 13, 1985), which enjoys common ownership and is incorporated herein by reference.

Positive and negative controls can be included in the assay of the present invention to ensure reliable results. A blank solid phase(s), to which no capture reagent has been attached, can be utilized as the negative reagent control. Positive controls can include a positive control for each analyte which control is tested separately, and a combined positive control wherein the presence of all analytes to be detected in the assay are determined.

It is contemplated and within the scope of the present invention that polynucleotides, i.e., DNA and/or RNA sequences of an analyte can be assayed using the dioxetane compounds of the present invention and known amplification techniques.

For example, U.S. Pat. Nos. 4,683,195 and 4,683,202 teach a method of amplifying DNA sequences by using PCR. The protocols taught in these two patents and the method as described in the package insert of the commercially-available Gene-Amp™ kit (Document No. 55635-6/89, Perkin-Elmer/Cetus, Emeryville, Calif.) are now standard procedures in many molecular biology laboratories.

In PCR, two complementary polynucleotide strands are amplified by treating the strands with two oligonucleotide primers such that an extension product of each primer is synthesized which is complementary to each nucleic acid strand. The primers are selected such that the extension product of one primer forms a template for the synthesis of an extension product from the other primer once the extension product of the one primer is separated from the template. A chain reaction is maintained by a cycle of denaturing the primer extension products from their templates, treating the single-stranded molecule generated with the same primers to re-anneal, and allowing the primers to form further extension products.

The cycle is repeated for any many times as it takes to increase the target nucleic acid segments to a concentration where they can be detected.

The amplified target sequence can be detected by denaturing the double-stranded products formed by PCR, and treating those products with one or more reporter probes which hybridize with the extension products. The reporter probe may have a dioxetane compound of the present invention as a detectable label, and usually is added in excess. The unhybridized reporter probe, therefore, must be separated from the hybridized reporter probe by involving a separation step. In another method of detecting the extension products without reporter probe and a separation step, the extension products are detected by gels stained with ethidium bromide. The diagnosis can be confirmed by transferring the DNA to nitrocellulose and probing with a probe specific to the type suspected of being present in the sample.

The Ligase Chain Reaction (LCR) amplifies sections of DNA by copying the section of DNA, and copying the copies of that section of DNA, many times over. This method is described in European Patent Application No. 0 320 308 published Jun. 14, 1989, which is incorporated herein by reference. In this procedure, two probes (for example, A and B) complementary to immediately adjacent regions of a target sequence are hybridized and ligated. This ligated probe then is denatured away from the target, after which it is hybridized with two additional probes (A' and B') of sense opposite to the initial probes A and B. The secondary probes are themselves then ligated. Subsequent cycles of denaturation/hybridization/ligation create the formation of double-length probes of both sense (+) and antisense (−).

In LCR, the nucleic acid of the sample is provided either as single stranded DNA or as double-stranded DNA which is denatured to separate the strands. Four probes are utilized: the first two probes (A and B) are the so-called primary probes, and the second two probes (A' and B') are the so-called secondary probes. The first probe (A) is a single strand capable of hybridizing to a first segment of the primary strand of the target nucleotide sequence. The second probe (b) is capable of hybridizing to a second segment of the primary strand of the target nucleotide sequence. The 5' end of the first segment of the primary strand of the target is positioned relative to the 3' end of the second segment of the primary strand of the target to enable joining of the 3' end of the first probe to the 5' end of the second probe, when the probes are hybridized to the primary strand of the target nucleotide sequence. The third probe (A') is capable of hybridizing to the first probe, and the fourth probe (B') is capable of hybridizing to the second probe (B). The hybridized probes are ligated to form reorganized fused probe sequences. Then, the DNA in the sample is denatured to separate ligated probes from sample DNA. Successive cycles wherein the ligated probes and target DNA undergo the above-described process are performed to increase the amount of detectable DNA in the sample. The amount of cycles performed is dependent upon the sequence used and the sensitivity required of the test. Usually, the cycle can be repeated from 15 to 60 times. At least one of the probes can be conjugated to a signal generating compound.

If the four probes are conjugated to appropriate binding members such as the chemiluminescent dioxetane compounds of the present invention, the detection of amplified product can be accomplished using standard manual or automated immunoassay procedures known to those skilled in the art. These procedures include, for example, immunochromatography, ELISA, EIA and MEIA.

Hybridization also can be accomplished by following standard dot-, slot- or replica-blot procedures which are known to those in the art. The sequences can be labeled with an appropriate signal generating compound (label), which is capable of generating a measurable signal detectable by external means.

Test kits useful for detecting an analyte of interest in a test sample are also provided. These include a container containing a chemiluminescent dioxetane compound of the present invention and a means for generating a detectable chemiluminescent signal, wherein said means is an enzyme or a chemical.

The present invention will now be described by way of examples, which are meant to illustrate, but not to limit, the spirit and scope of the invention.

EXAMPLE 1

Preparation of 4-(3-tert-Butyldimethylsilyloxy-4-methoxyphenyl)-4-methoxyspiro[1,2-dioxetane-3,2'-adamantane]

Step 1: Preparation of Methyl 3-hydroxy-4-methoxybenzoate

A mixture of 3-hydroxy-4-methoxybenzoic acid (Aldrich, 10 g, 59.5 mmol), methanol (250 ml) and concentrated sulfic acid (1 ml) was stirred overnight and the product was poured into a mixture of sodium bicarbonate and ice. The aqueous mixture was then extracted three times with ethyl acetate. The resulting organic layers were combined, washed with water and brine, and dried over anhydrous magnesium sulfate. Rotary evaporation of the solution gave 9.5 g of the desired product as a colorless oil. NMR (δ):3.89 (s, 3H), 3.95 (s, 3H).

Step 2: Preparation of Methyl 3-tert-butyldimethylsilyloxy-4-methoxybenzoate)

A mixture of methyl 3-hydroxy4-methoxybenzoate (120 mg, 0.66 mmol, prepared in Step 1, above), tert-butyldimethylsilyl chloride: (109 mg, 0.72 mmol), imidazole (98 mg, 1.24 mmol) and dimethylformamide (DMF, 2 ml) was stirred at room temperature over night. Extractive workup with hexane gave 90 mg of methyl 3-tert-butyldimethylsilyloxy-4-methoxybenzoate. NMR(δ): 0.18 (s, 3H), 1.00 (s, 9H),3.88 (s, 3H), 3.89 (s, 3 H).

Step 3: Preparation of [(3-tert-Butyldimethylsilyloxy-4-methoxyphenyl) methoxymethylene]adamantane 2-Adamantanone (Aldrich, 55 mg, 0.37 mmol) and methyl 3-tert-butyldimethylsilyloxy-4-methoxybenzoate (90 mg, 0.30 mmol, prepared as in Step 2, above) were mixed and dissolved in 0.9 ml of anhydrous tetrahydrofuran (THF). Lithium aluminum hydride (51 mg, 1.34 mmol) was added with stirring to an ice-cold mixture of titanium trichloride (Aldrich, 440 mg, 2.85 mmol) in THF under nitrogen. The ice-bath was removed and triethylamine was added to the mixture. After refluxing for 1 hr, the 2-adamantanone-methyl 3-tert-butyldimethylsilyloxy-4-methoxybenzoate mixture was introduced via a syringe pump over 5 hr period. The mixture was refluxed and stirred for 4 additional hours. After cooling to room temperature, the black mixture was partitioned three times between saturated sodium bicarbonate solution and ethyl acetate. The combined extracts were washed with water and brine and dried over magnesium sulfate. The solution was evaporated to give a tan solid which was flash-chromatographed over silica gel. Elution with hexane/ethylacetate (15:1) afforded 26 mg of |(3-tert-butyldimethylsilyloxy-4-methoxyphenyl) methoxy methylene|adamantane as a colorless oil. NMR($\delta$): 0.18 (s. 6H), 1.00 (s. 9H), 3.30 (s. 3H), 3.85 (s. 3H).

Step 4: Preparation of 4-(3-tert-Butyldimethylsilyloxy-4-methoxyphenyl)-4-methoxyspiro|1.2-dioxetane-3.2'-adamantane|

Oxygen was gently bubbled through a mixture of the |(3-tert-butyldimethylsilyloxy-4-methoxyphenyl)methoxy methylene|adamantane (26 mg. prepared as described in Step 3. above) and SENSITOX (35 mg. prepared according to the method of Schaap. et al., *J. Am. Chem. Soc.*, Vol. 97 (13): 3741, 1975) in methylene chloride irradiated with a high pressure sodium lamp. After the mixture was stirred at ice temperature for 2 hr the light was turned off and the oxygenation terminated. The catalyst was removed by filtering through cotton and the filtrate stripped to give 25 mg of 4-(3-tert-butyldimethylsilyloxy-4-methoxyphenyl) 4methoxyspiro|1.2-dioxetane-3.2'-adamantane| as a light pink oil. DCI $NH_3$ MS m/e: 447 ($M^+$+1).

EXAMPLE 2

Preparation of 4-(3-phosphate-4-methoxyphenyl)-4-methoxyspiro|1.2-dioxetane-3.2'-adamantane|. tetraethylammonium salt Step 1: Preparation of |(3-Hydroxy-4-methoxy phenyl)methoxymethylene)| adamantane After stirring at room temperature for 30 min a mixture of 4-(3-tert-butyldimethylsilyloxy-4-methoxyphenyl)-4-methoxyspiro|1.2-dioxetane-3.2'-adamantane| (1.23 g. prepared as described in Step 3. above) and 10 ml of 1M tetra-n-butylammonium fluoride was partitioned three times between water and ether. The combined organic layers were washed with water and brine and evaporated to give an oil which was flash chromatographed over silica gel. The column was eluted with hexane/ethyl acetate to give 682 mg of a viscous oil. Approximately 80 mg of the oil was applied to a silica gel preparative thin layer chromatography plate (20 cm×20 cm×2 mm) which was developed with hexane/ethyl acetate (2:1) to give a broad band. The upper and lower portions of the band were scraped and separately eluted with methanol. NMR analysis showed that the two portions were identical and consistent with the structure of the desired compound. The two portions were thus combined to give 57 mg of |(3-hydroxy-4-methoxyphenyl)methoxymethylene| adamantane as the final product. NMR($\delta$): 3.30 (s, 3H), 3.91 (s, 3H).

Step 2: Phosphorylation of |(3-Hydroxy-4-methoxyphenyl) methoxymethylene)| adamantane A solution of |(3-hydroxy-4-methoxyphenyl) methoxymethylene)| adamantane (prepared as described in Example 1, 57 mg) in 2 ml pyridine was added dropwise with stirring to an ice cooled solution of phosphoryl chloride in pyridine (85 mg in 2 ml pyridine). After the addition was complete, the ice bath was removed and the mixture was stirred at ambient temperature for 1 hr. Water was added and the aqueous mixture was titrated with 1.45 ml of 20% tetraethylammonium hydroxide (to pH 8.0). The resulting mixture was extracted three times with chloroform. The organic layers were combined, washed with brine, and dried with magnesium sulfate. TLC (silica gel. hexane/ethyl acetate in a 2:1 ratio) indicated only a spot on the origin. Rotary evaporation of the solution gave the title compound as a tan powder (75 mg).

Step 3: Preparation of 4-(3-phosphate-4-methoxyphenyl)-4-methoxyspiro|1.2-dioxetane-3.2'-adamantane|. tetraethylammonium salt Oxygen was gently bubbled through a mixture of the |(3-tetraethyl ammonium-phospho-4-methoxyphenyl) methoxy methylene|adamantane (20 mg, prepared as described in Step 1, above) and SENSITOX (36 mg, prepared as described in Example 1, above) in methylene chloride irradiated with a high pressure sodium lamp. After the mixture was stirred at ice temperature for 2 hr the light was turned off and the oxygenation terminated. The catalyst was removed by filtering through cotton and the filtrate stripped to give 10 mg of the title compound as an oily residue. Electrospray mass spec.calcd. for monotetraethylammonium salt, m/z=541; observed 542 ($M^{3o}$ +1)

EXAMPLE 3

Preparation of 4-(3-tert-Butyldimethylsilyloxy-4-methoxyphenyl)4-methoxyspiro {1.2-dioxetane-3.2'-(1'.7'.7'-trimethylbicyclo|2.2.1|heptane)}

Step 1: Preparation of |(3-tert-Butyldimethylsilyloxy-4-methoxyphenyl) methoxymethylene|(1'.7'.7'-trimethyl bicyclo|2.2.1| heptane)

Methyl 3-tert-butyldimethylsilyloxy-4-methoxybenzoate (170 mg, 0.57 mmol, prepared in Example 1, Step 2 above) and (1R)-(+)-camphor (Aldrich, 120 mg, 0.79 mmol) were mixed and dissolved in anhydrous tetrahydrofuran (THF, 1.98 ml) and 15 coupled as described in the procedure of Example 1, Step 3, above, by using titanium trichloride (1.9 g, 12.32 mmol), LAH (0.22 g, 5.80 mmol) and THF (13.8 ml). The product was purified on a preparative TLC plate (silica gel). Development with hexane/ethyl acetate (10:1) gave the title compound as a mixture of two isomers (58 mg). NMR($\delta$): 0.18 (s, 6H), 1.00 (s, 15H), 1.29 (s, 3H), 3.23 (s, 1H, minor isomer), 3.30 (s, 2H, major isomer), 3.85 (s, 3H).

Step 2: Preparation of 4-(3-tert-Butyldimethylsilyloxy-4-methoxyphenyl)4-methoxyspiro {1.2-dioxetane-3.2'-(1'.7'.7'-trimethylbicyclo|2.2.1|heptane)}

[(3-tert-Butyldimethylsilyloxy-4-methoxyphenyl) methoxymethylene|camphorane (58 mg, prepared described) was photooxidized with SENSITOX (80 mg, prepared as described above) as described in Example 2, step 3. After the mixture was stirred at ice temperature for 2 hr the light was turned off and the oxygenation terminated. The catalyst was removed by filtering through cotton and the filtrate stripped to give the title compound (55 mg) as an oily residue. DCI $NH_3$ MS m/e: 449 ($M^+$+1).

EXAMPLE 4

Preparation of 4-(3-tert-Butyldimethysilyloxy-4-methoxyphenyl)-4-(4-hydroxybutyloxy)spiro{1.2-dioxetane-3.2'-(1'.7'.7'-trimethylbicyclo[2.2.1] heptane)}

Step 1: Preparation of 3-(tert-Butyldimethylsilyloxy)-4-methoxybenzoic acid

A mixture of 3-hydroxy-4-methoxybenzoic acid (6.726 g, 40 mmol), tert-butyldimethylsilyl chloride (13.26 g, 88 mmol), imidazole (10.893 g, 160 mmol) and DMF (40 mL) was stirred at room temperature for 18 hr. Hexane was added and the resulting mixture washed with water. The aqueous layer was reextracted two times with hexane and the extracts added to the hexane layer from the first extraction. The combined extracts were washed with small amount of water. During the washing some precipitate formed. The organic phase, together with the precipitate, was dissolved in small amount of methanol and rotary evaporated. The residue was taken into methanol (100 ml) and stirred at room temperature with potassium carbonate (10 g) and water (3 ml) for 1.5 hr. A mixture of ethyl acetate and crushed ice was added and the mixture was carefully acidified with dilute hydrochloric acid (the final pH of the aqueous layer was 3.5). The organic phase was separated and the aqueous layer extracted two times with ethyl acetate. The combined extracts were washed with a mixture of brine and water (1:1) and dried. TLC (silica gel, hexane/ethyl acetate=2:1) of the product gave one spot having an Rf of 0.2. NMR($\delta$): 0.18 (s, 6H), 1.00 (s, 9H), 3.90 (s, 3H).

Step 2: Esterification of 3-(tert-Butyldimethylsilyloxy)-4-methoxybenzoic acid To a mixture of 3-(tert-butyldimethylsilyloxy)-4-methoxybenzoic acid (2.82 g, 10 mmol, prepared as described in Example 4, Step 1, above) and 1,4-butanediol (4.5 g, 55 mmol) in methylene chloride (20 mL) was added dicyclphexylcarbodiimide (DCC, 2.27 g, 11 mmol), followed by 4-dimethylaminopyridine (DMAP, 122 mg, 1 mmol). The mixture was stirred at room temperature for 18 hr. Water was added and the aqueous mixture was extracted three times with ethyl acetate. The combined organic layers were washed with sodium bicarbonate, water, and brine, successively. After drying over anhydrous magnesium sulfate, the solution was evaporated to give a crude material which was flash chromatographed over silica gel. Elution with hexane/ethyl acetate (2:1) gave a colorless oil (1.85 g). NMR($\delta$): 0.18 (s, 6H), 1.00 (s, 9H), 3.74 (t, 2H), 3.89 (s, 3H), 4.35 (t, 1H).

Step 3: Preparation of 4-(3-tert-Butyldimethylsilyloxy-4-methoxyphenyl)-4-(4-hydroxybutyloxy)methylene-2-(1',7',7'-trimethylbicyclo[2.2.1]heptane)

Titanium trichloride (4.47 g, 29 mmol), lithium aluminum hydride (0.56 g, 14.75 mmol), THF (33 ml), triethylamine (2.24 ml, 1.63 g, 16 mmol), (1R)-(+)-camphor (304.48 mg, 2 mmol), 4-(3-tert-butyldimethylsilyloxy)-hydroxybutyl-4-methoxybenzoate (448 mg, 1.264 mmol, prepared as described in Step 2, above) and THF (5 ml) were mixed as described in Example 1, Step 3. The reaction mixture was then poured into a solution of ice water and sodium bicarbonate. The organic layer was separated and the aqueous layer extracted with two additional batches of ethyl acetate. The organic layers were combined, washed with water and brine, and dried over magnesium sulfate. A portion of the solution was evaporated to give an oil which was fractionated on a prep TLC plate and developed with hexane/ethyl acetate (2:1) to give the titled compound as a mixture of two isomers. The remaining material was chromatographed over a silica gel column and eluted with hexane/ethyl acetate (2:1) to give 80 mg of a colorless oil. NMR($\delta$): 0.18 (s, 6H), 1.00 (s, 12H), 3.30–3.50 (2t, 2H), 3.80 (s, 3H).

Step 4: Preparation of 4-(3-tert-Butydimethylsilyloxy-4-methoxy)phenyl-4-(4-hydroxybutylspiro{1,2-dioxetane-3,2'-(1', 7',7'-trimethylbicyclo[2.2.1]heptane)}.

To the isomeric mixture obtained in Step 3, above (24 mg) was added 45 mg of SENSITOX and 3 ml of methylene chloride. The mixture was oxygenated as described in Example 2, Step 3 to give the title compound. DCI NH$_3$ MS m/e: 507 (M$^{30}$+1).

EXAMPLE 5

Preparation of 4-(3-tert-butyldimethylsilyloxy-4-methoxy)phenylspiro{4.1'-(epoxymethano)-1,2-dioxetane-3,2'-(1',7',7'-dimethylbicyclo[2.2.1]heptane)}

Step 1: Preparation of 7,7-Dimethyl-2-hydroxy-1-hydroxymethyl bicyclo[2.2.1]heptane To an ice-cooled mixture of lithium aluminum hydride (4 g, 105.4 mmol) in ether was added dropwise a solution of camphorsulfonyl chloride (10 g, 39.88 mmol) and ketopinic acid, prepared as described in Step 1, above. After the addition was complete, the ice bath was removed and the mixture was stirred at ambient temperature for 2 hrs. The mixture was cooled again and wet ether was added cautiously. When the violent reaction subsided, water was added. The mixture was then extracted three times with ethyl acetate. The combined extracts were washed with water and brine and dried over anhydrous magnesium sulfate. Evaporation of the solution gave 4.8 g of a white powder. NMR($\delta$): 0.90 (s, 3H), 1.20 (s, 3H).

Step 2: Preparation of 7,7-Dimethyl-1-hydroxymethyl-2-oxobicyclo[2.2.1]heptane To a stirred solution of the diol (632 mg, 3.71 mmol, prepared in Step 2, above) in 3 ml of glacial acetic acid was added 5 mL of sodium hypochlorite solution at room temperature. After stirring for 2 hrs., an additional 2.5 ml of sodium hypochlorite was added and the mixture allowed to stir overnight. After diluting with water the aqueous mixture was extracted three times with ethyl acetate. The combined extracts were washed with sodium bicarbonate, water and brine. Rotary evaporation of the solution gave a crude product (516 mg) which showed one spot on TLC (silica gel, hexane/ethyl acetate (2:1), Rf=0.4). NMR ($\delta$) 1.00 (s, 3H), 1.01 (s, 3H), 3.56 (q, 2H).

Step 3: Preparation of 1-{3-tert-Butyldimethylsilyloxy-4-methyoxy)benzoyloxymethyl-7,7-dimethylbycyclo[2.2.1]heptan-2-one To a mixture of the keto alcohol (503 mg, 2.99 mmol, prepared in Step 3, above) and 3-tert-butyldimethylsiloxy-4-methoxybenzoic acid, (prepared in Example 4, Step 1.768 mg, 2.72 mmol) in methylene chloride was added DCC (617 mg, 2.99 mmol) followed by dimethylaminopyridine (33 mg, 0.27 mmol). The mixture was stirred at room temperature for 18 hrs. The reaction mixture was partitioned between water and ether, and the combined ether extracts washed with water and brine. After drying over magnesium sulfate the solution was evaporated to give a crude product which was chromatographed over silica gel. Elution with hexane/ethyl acetate (5:1) gave 510 mg of the title compound. NMR($\delta$): 0.17 (s, 6H), 1.00 (s, 9H), 1.05 (s, 3H), 1.14 (s, 3H), 3.89 (s, 3H), 4.49 (t, 2H).

Step 4: Preparation of 3-(3-tert-butyldimethylsilyloxy-4-methoxy)phenyl-4a, 6a-Dimethylmethano-1H, 5H, 6H-benzo[c]furan The ketoester (250 mg, 0.58 mmol, prepared in Step 4, above) was cyclized as described in Example 1, Step 3. The crude product was elution with hexane/ethyl acetate (20:1) to give 37 mg of the desired product. NMR(δ): 0.18 (s, 6H), 0.95 and 1.00 (two singlets, 15H), 3.80 s, 3H), 4.18 (q, 2H).

Step 5: Preparation of 4-(3-tert-butyldimethylsilyloxy-4-methoxy)phenylspiro{4,1'-(epoxymethano)-1,2-dioxetane-3,2'-(7',7'-dimethylbicyclo|2.2.1|heptane)}

The enol ether (37 mg, 0.092 mmol, prepared in Step 4, above) was photooxygenated in the presence of SENSITOX as described in Example 1, above, to yield the title compound (35 mg). DCI NH$_3$ MS m/e: 433 (M$^+$+1).

EXAMPLE 6

Preparation of 4-(3-tert-Butyldimethylsilyloxy-4-methylphenyl)-4-methoxyspiro{1,2-dioxetane-3,2'-(1',7',7'-trimethylbicyclo|2.2.1|heptane)}

Step 1: Preparation of Methyl 3-tert-Butyldimethylsilyloxy-4-methylbenzoate

The title compound was prepared in two steps from 3-hydroxy-4-methylbenzoic acid according to a procedure similar to that as described in Example 1, Steps 1 and 2, for the preparation of the corresponding methoxyphenyl derivative. NMR(δ): 0.25 (s, 6H), 1.00 (s, 9H), 2.45 (s, 3H) and 3.85 (s, 3H).

Step 2: 4-(3-tert-butyldimethylsilyloxy-4-methylphenyl)-4-methoxymethylene-2'-(1',7',7'-trimethylbicyclo|2.2.1]heptane)

The title compound was prepared from methyl 3-tert-butyldimethylsilyloxy-4-methylbenzoate obtained above according to the procedure as described in Example 3, Steps 1 and 2, for the preparation of the corresponding methoxyphenyl derivative. NMR(δ): 0.25 (s, 6H), 1.00 (s, 15H), 2.20 (s, 3H), 3.30 (s, 1H, major isomer), 3.50 (s, 2H, minor isomer).

Step 3: Preparation of 4-(3-tert-Butyldimethylsilyloxy-4-methylphenyl)-4-methoxyspiro{1,2-dioxetane-3,2'-(1',7',7'-trimethylbicyclo|2.2.1|heptane)}

The title compound was prepared from 4-(3-tert-butyldimethylsilyloxy-4-methylphenyl)-4-methoxymethylene -2'-1',7',7'-trimethylbicyclo|2.2.1| heptane) (prepared in Step 2, above) according to the procedure as described in Example 3, Step 2 for the preparation of the corresponding methoxyphenyl derivative. DCI NH$_3$ MS m/e: 433 (M$^{30}$+1).

EXAMPLE 7

Chemical Triggering of 4-(3-tert-Butyldimethylsilyloxy-4-methoxyphenyl)-4-methoxyspiro|1,2-dioxetane-3,2'-adamantane|

Figure 1A:
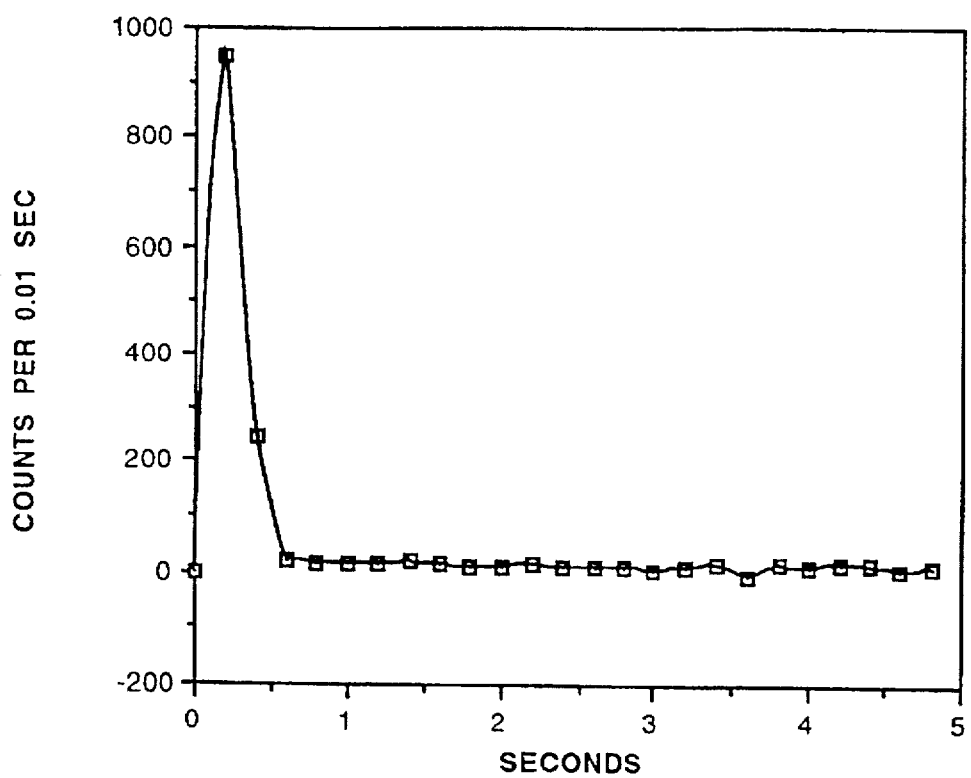
FIG. 1A is a graph showing the time profile of the chemical triggering of 4-(3-tert-butyldimethylsilyloxy-4-methoxyphenyl)-4-methoxyspiro[1,2-dioxetane-3,2'-adamantane] with tetra-n-butylammonium fluoride in THF.
Figure 1B:
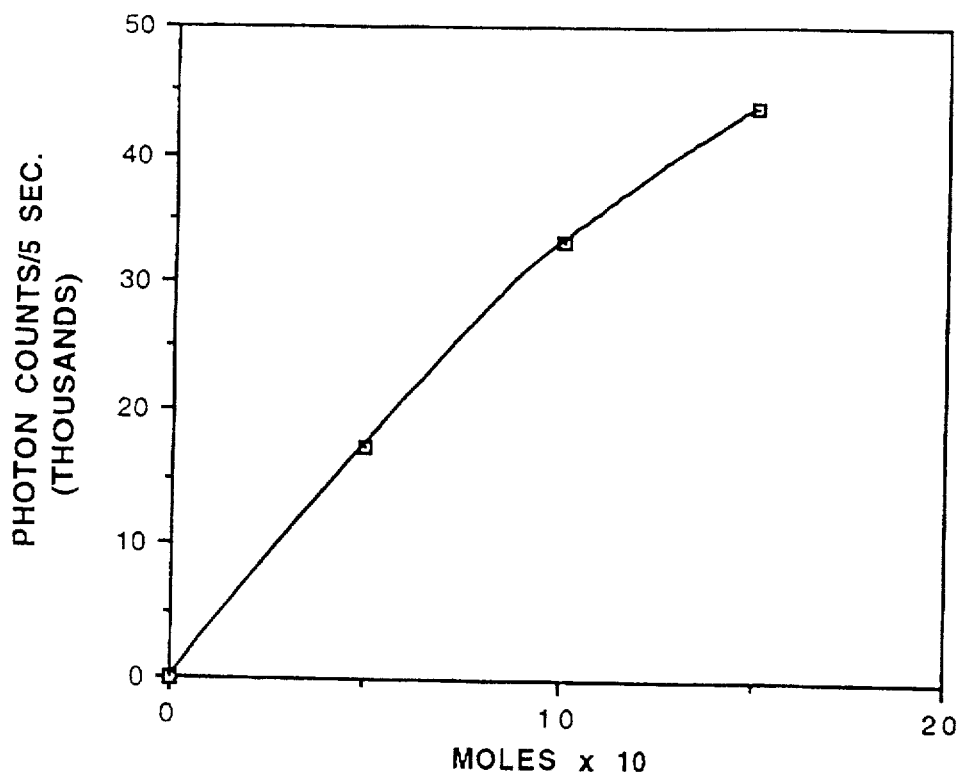
FIG. 1B shows the level of detection of 4-(3-tert-butyldimethylsilyloxy-4-methoxyphenyl)-4-methoxyspiro [1,2-dioxetane-3,2'-adamantane] in THF triggered by tetra-n-butylammonium fluoride in THF.

The title dioxetane (prepared in Example 1) was dissolved in THF to the amounts indicated in Table I, below placed in a photon counting luminometer. Darkcount was monitored. When the darkcount was stabilized, trigger solution comprising 1M tetra-n-butylammonium fluoride in THF (100 μl) was injected into the reaction mixture. The chemiluminescence reaction was monitored for 5 seconds. The specific activity is calculated in Table 1 and the chemiluminescence profile and sensitivity are shown in FIGS. 1A and 1B, respectively.

TABLE 1

Specific Activity of 4-(3-tert-Butyldimethylsilyloxy-4-methoxyphenyl)-4-methoxyspiro|1,2-dioxetane-3,2-adamantane|

| Amount | Net Counts/5 sec | Specific Activity |
|---|---|---|
| 5 × 10$^{-18}$ moles | 17467 | 3.5 × 10$^{21}$ |
| 10 × 10$^{-18}$ moles | 33240 | 3.3 × 10$^{21}$ |
| 15 × 10$^{-18}$ moles | 43787 | 2.9 × 10$^{21}$ |

EXAMPLE 8

Figure 2:
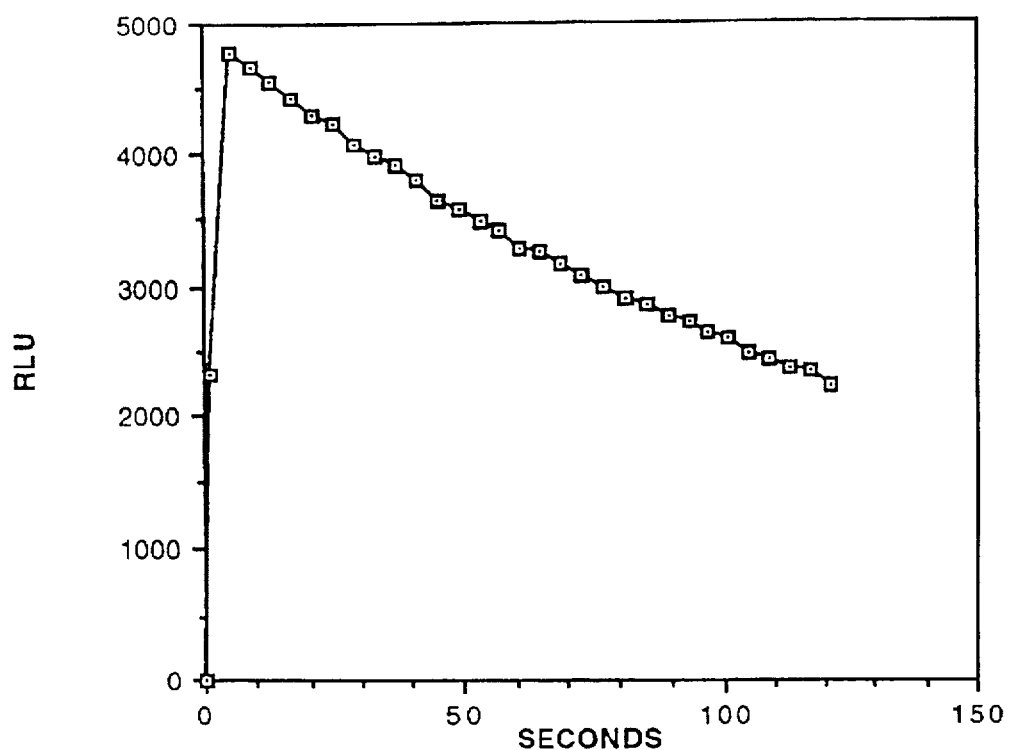
FIG. 2 is the chemiluminescence time profile of 4-(3-phosphate-4-methoxyphenyl)-4-methoxyspiro[1,2-dioxetane-3,2'-adamantane], tetraethylammonium salt triggered by alkaline phosphatase.

Enzymatic Triggering of 4-(3-phosphate-4-methoxyphenyl)-4-methoxyspiro|1,2-dioxetane-3,2'-adamantane|, tetraethylammonium salt Ninety microliters of 0.4 mM solution of the title dioxetane (prepared in Example 2) in 0.05M carbonate pH 9.5 containing 1 mM MgCl$_2$ was mixed with alkaline phosphatase (enzyme amounts in Table 2, below) and immediately placed in a photon counting luminometer to monitor the photon output for at least 2 minutes. The photon output from the solution without the enzyme was the control. The time profile of alkaline phosphatase-triggered decomposition of the title compound is shown in FIG. 2 and Table 2, below. The delectability of alkaline phosphatase indicates as little as 10$^{-16}$ moles of enzyme can be detected.

TABLE 2

Time Profile of Enzyme-Triggered 4-(3-phosphate-4-methoxyphenyl)-4-methoxyspiro|1,2-dioxetane-3,2'-adamantane|, tetraethylammonium salt

| Enzyme | counts/sec t = 0' | counts/sec t = 2' |
|---|---|---|
| 8 × 10$^{-19}$ mole | 56 | 20 |
| 8 × 10$^{-16}$ mole | 156 | 41 |
| 8 × 10$^{-14}$ mole | 2443 | 2344 |

EXAMPLE 9

Chemical Triggering of 4-(3-tert-Butyldimethylsilyloxy-4-methoxyphenyl)-4-methoxyspiro {1 2-dioxetane-3,2'-(1',7',7'-trimethylbicyclo|2.2.1|heptane)

Figure 3:
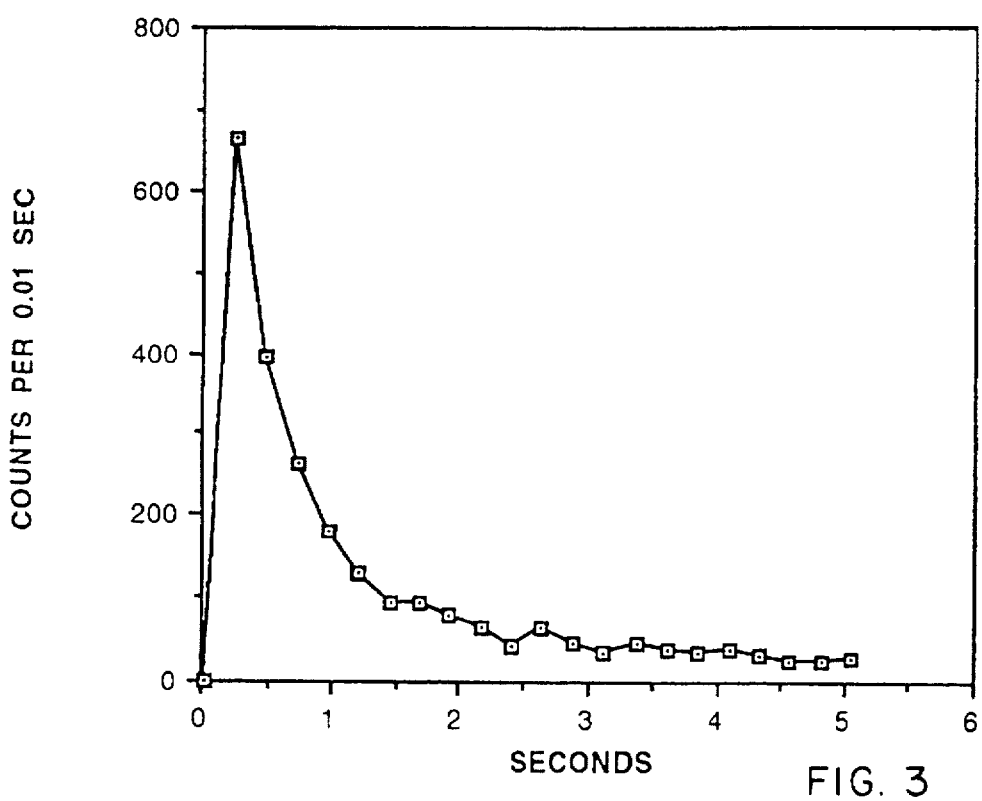
FIG. 3 is a graph showing the time profile of the chemical triggering of 4-(3-tert-butyldimethylsilyloxy-4-methoxyphenyl)-4-methoxyspiro{1,2-dioxetane-3,2'-(1',7',7'-trimethylbicyclo[2.2.1]heptane)} with tetra-n-butylammonium fluoride in THF.

One hundred microliters of a solution of the title dioxetane (prepared in Example 3) in THF containing 2.0×10$^{-14}$ moles of the compound was placed in a photon counting luminometer. Darkcount was monitored. When the darkcount was stabilized, trigger solution comprising 1M tetra-n-butylammonium fluoride in THF (100 μl) was injected into the reaction mixture. The chemiluminescence reaction was monitored for 6 seconds. The net chemiluminescent count was 67647 for a specific activity was calculated at 3.4×10$^{18}$ for 2×10$^{-14}$ moles. The chemiluminescence profile is shown in FIG. 3.

EXAMPLE 10

Chemical Triggering of 4-(3-tert-butyldimethylsilyloxy-4-methoxy)phenylspiro{4,1'-(epoxymethano)-1,2-dioxetane-3,2'-(7',7'-dimethylbicyclo|2.2.1|heptane)}

Figure 4:
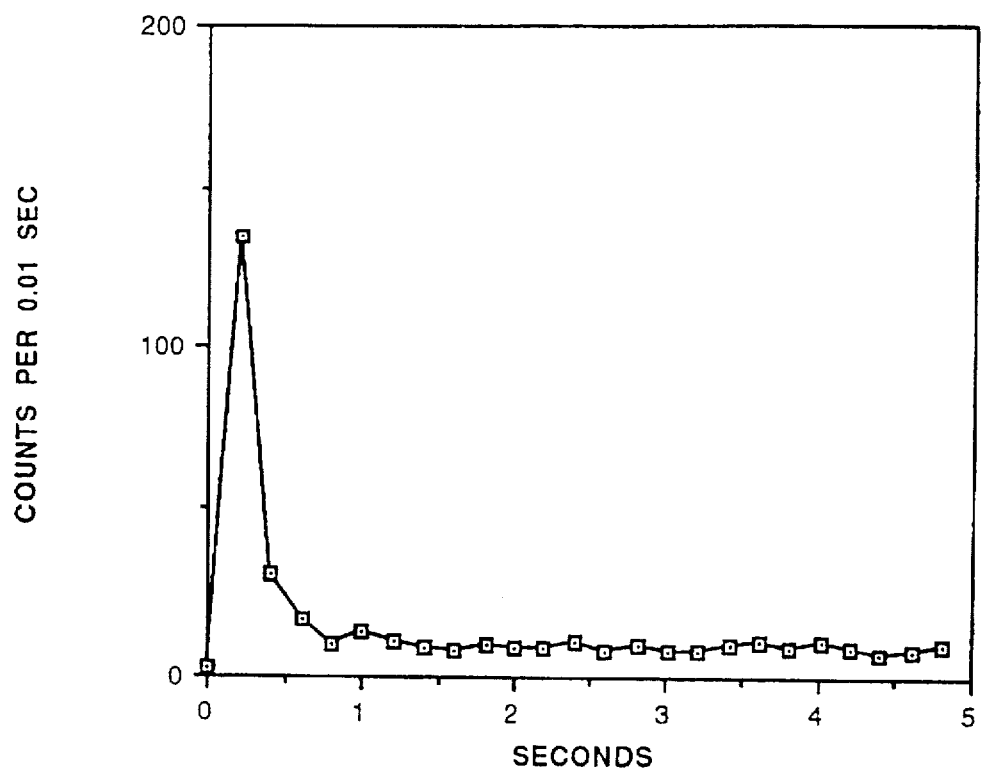
FIG. 4 is a graph showing the time profile of the chemical triggering of 4-(3-tert-butyldimethylsilyoxy-4-methoxy) phenylspiro{4,1'-(epoxymethano)-1,2-dioxetane-3,2'-(7',7'-dimethylbicyclo[2.2.1]heptane)} with tetra-n-butylammonium fluoride in THF.

One hundred microliters of a solution of the title dioxetane (prepared in Example 5) in THF containing 2×10$^{-18}$ moles was placed in a photon counting luminometer. Darkcount was monitored. When the darkcount was stabilized, trigger solution comprising 1M tetra-n-butylammonium fluoride in THF (100 ml) was injected into the reaction mixture. The chemiluminescence reaction was monitored for 50 seconds. The specific activity was calculated at $4.0 \times 10^{21}$ for $2 \times 10^{-18}$ moles. The chemiluminescence profile is shown in FIG. 4.

EXAMPLE 11

Chemical Triggering of 4-(3-tert-Butyldimethylsilyloxy-4-methoxyphenyl)-4(4-hydroxybutyloxy)spiro{1,2-dioxetane-3,2'-(1',7',7'-trimethylbicyclo[2.2.1]heptane)}

One hundred microliters of a solution of the title dioxetane (prepared in Example 4) in THF containing $2 \times 10^{-16}$ moles was placed in a photon counting luminometer. Darkcount was monitored. When the darkcount was stabilized, trigger solution comprising 1M tetra-n-butylammonium fluoride in THF (100 µl) was injected into the reaction mixture. The net chemiluminescence count was 84621 for 50 seconds for a specific activity of $4.2 \times 10^{20}$.

EXAMPLE 12

Enzyme Catalyzed Chemiluminescence Immunoassay For Human Thyrotropin (hTSH) Using 4-(3Phosphate-4-Methoxyphenyl)-4-Methoxyspiro[1,2-Dioxetane-3,2'-Adamantane], Tetraethyl Ammonium Salt.

Instrument: The Abbott Prism™ Multichannel Heterogeneous Chemiluminescence Immunoassay Analyzer described by Khalil et al, *Clinical Chemistry*, 37, 1540–1547 (1991A) is used. The disposable reaction tray described by Khalil et al, *Clinical Chemistry*, 37, 1612–1617 (1991B) is used for incubation and separation of the immunological reaction mixture. Additional details of the instrument are given by Khalil, et al, U.S. Pat. No. 5,089,424. Additional details on the disposable reaction tray are disclosed in U.S. Pat. No. 5,006,309.

Reagents:

Capture Antibody: A mouse monoclonal antibody specific for the beta subunit of hTSH is coated onto a carboxylated latex by a covalent attachment method and is available from Abbott Laboratories as the capture antibody in the IMx® Ultrasensitive hTSH kit, list number 3A62-20.

Enzyme Conjugate: An affinity purified sheep polyclonal antibody specific for hTSH is coupled to calf intestinal alkaline phosphatase. This reagent is available as the label in the IMx® Ultrasensitive hTSH kit, list number 3A62-20; it is used at a concentration of at least 1 ug/mL.

Substrate: The substrate composition described in Example 8, above is used.

Transfer Buffer: MEIA™ Diluent Buffer, list number 8374-04, available from Abbott Laboratories is used as the transfer buffer and initial wash buffer.

Wash Buffer: The Wash Buffer from the IMx® Ultrasensitive TSH kit, list number 3A62-20 is used.

Protocol:

The TSH protocol of Khalil et al (1991A), supra is used.

| STEP | TIME(MIN) | ACTION |
|---|---|---|
| 1 | 0 | Dispense 30 µL microparticles |
| 2 | 9.6 | Dispense 100 µL sample |
| 3 | 28.8 | Transfer with 600 µL transfer buffer |
| 4 | 38.4 | Dispense 30 µL enzyme conjugate |
| 5 | 67.2 | Wash with 100 µL wash buffer |
| 6 | 76.8 | Trigger with 85 µL substrate Immediately read for 6 seconds |

At time zero, 30 microliters of capture antibody coated microparticles is dispensed into an incubation well of a Prism™ disposable. The trays are warmed to about 37° C. At 9.6 minutes 100 uL of sample (or calibrator or control) is added. The mixture is incubated for 19.2 minutes at 37° C. At 28.8 minutes elapsed time, the reaction mixture is transferred to the pad of the reaction tray with a jet of 600 uL of transfer buffer; the buffer also provides a first wash step. At 38.4 minutes, 30 uL of enzyme conjugate is added to the reacted particles trapped in the pad of the disposable. The conjugate is incubated with the particles for 28.8 minutes at 37 degrees C.; the particles and pad are the washed with 100 UL wash buffer in two 50 uL aliquots (elapsed time 67.2 minutes). After an additional 9.6 minutes of incubation, the reaction is read out by adding 85 uL of dioxetane substrate to the pad. Photon counting is initiated immediately and the total photon counts over the 6 seconds are accumulated and stored in memory. In the case of calibrators, a standard curve is constructed; for controls or patient unknowns, the total counts over the 6 second read period are compared to the standard curve and the concentration of the unknown computed.

EXAMPLE 13

Direct Chemiluminescence Immunoassay For-hTSH Using 4-(3-Tert-Butyldimethylsilyloxy-4-Methoxyphenyl)-4-(4-Hydroxybutyloxy)Spiro{1,2-Dioxetane-3,2'-(1',7',7'-Trimethylbicylo[2.2.1] Heptane)}

Instrument And Disposable: The Instrument And Disposable Described In Example 12 Are Used.

REAGENTS:

Capture Antibody coated onto latex microparticles of Example 12 is used.

Chemiluminescent Conjugate: The affinity purified sheep polyclonal antibody of Example 12 is labeled with the title dioxetane and used for the indicator reagent. The labeling is performed in a two step process.

Activation of the title compound is achieved by reacting the alcohol portion of the compound with phosgene to form the chloroformate derivative. Two (2) mg of the compound (4 micromoles) are dissolved in 0.5 mL of tetrahydrofuran (THF) and mixed with 0.5 mL of 10% phosgene in benzene (over 100 mole excess). The reaction is allowed to proceed at room temperature for 2.5 hours and then the solvents are removed under a gentle stream of nitrogen. The residue is taken up with 200 uL of THF.

Reaction with the affinity purified sheep anti-TSH is performed in 0.1M NaHCO$_3$ titrated to pH 9.0 with 1.0M NaOH. The antibody concentration is adjusted to 1 mg/mL in the carbonate buffer. Two (2.0) mL of the antibody solution is placed in a vial and mixed with a magnetic stirrer as the title dioxetane chloroformate in THF is added in 4 aliquots of 50 μL each at thirty minute intervals; the sample is kept at room temperature for an additional thirty minutes after the last addition.

Purification of the conjugate is by Sephadex G25 exclusion chromatography. Following the reaction above, the entire contents of the vial is applied to a 20 mL 20 column of Sephadex G25 equilibrated with phosphate buffered saline (PBS) at pH 7.4. The conjugate is eluted with the same buffer and 1 mL fractions are collected. Fractions having an A280 greater than 0.05 A are pooled as the conjugate, the concentration of the pool is estimated using an extinction coefficient of 1.4 A/mL/mg, and are stored at 2–8 degrees C. in the presence of 10 mg/mL fish gelatin. The conjugate is used at about 1 ug/mL and is diluted into PBS containing 10 mg/mL fish gelatin.

Trigger reagent: 1M tetra-n-butylammonium fluoride in THF, obtained from Aldrich Chemical Company, Milwaukee, Wis. 53233, is used as the trigger.

Protocol:

The TSH protocol of Khalil et al (1991A), supra, is used.

| STEP | TIME(MIN) | ACTION |
|------|-----------|--------|
| 1 | 0 | Dispense 30 μL microparticles |
| 2 | 9.6 | Dispense 100 μL sample |
| 3 | 28.8 | Transfer with 600 μL transfer buffer |
| 4 | 38.4 | Dispense 30 μL dioxetane conjugate |
| 5 | 67.2 | Wash with 100 μL wash buffer |
| 6 | 76.8 | Trigger with 100 μL trigger Immediately read for 6 seconds |

At time zero, 30 microliters of capture antibody coated microparticles are dispensed into an incubation well of a Prism™ disposable. The tray is warmed to about 37° C. At 9.6 minutes 100 μL of sample (or calibrator or control) is added to the well. The mixture is incubated for 19.2 minutes at 37. At 28.8 minutes elapsed time, the reaction mixture is transferred to the pad of the reaction tray with a jet of 600 μL of transfer buffer; the buffer also provides a first wash step. At 38.4 minutes, 30 μL of dioxetane conjugate is added to the reacted particles trapped in the pad of the disposable. The conjugate is incubated with the particles for 28.8 minutes at 37° C.; the particles and pad are then washed with 100 μL wash buffer in two 50 μL aliquots (elapsed time 67.2 minutes). After an additional 9.6 minutes of incubation, the reaction is read out by adding 100 μL 1.0M tetra-n-butylammonium fluoride in THF to the pad. Reading the chemiluminescence output is initiated immediately and the total photon counts over 6 seconds are accumulated and stored in memory. In the case of calibrators, a standard curve is constructed; for controls or patient unknowns, the total counts over the 6 second read period are compared to the standard curve and the concentration of the unknown computed.

It will be appreciated by those skilled in the art that many of the concepts of the present invention are equally applicable to other types of binding assays. The embodiments described and presented are intended as examples rather than limitations. Thus, the description of the invention is not intended to limit the invention of the particular embodiments disclosed, but it is intended to encompass all equivalents and subject matter with the spirit and scope of the invention as described above and as set forth in the following claims.

What is claimed is:

1. A competitive assay for determining the presence and/or amount of analyte in a test sample, comprising:

(a) contacting the test sample suspected of containing the analyte and a control sample free of the analyte with a solid phase to which an analyte-specific binding member has been attached and an indicator reagent capable of generating a measurable signal comprising (i) said analyte or analyte derivative of said analyte and (ii) a chemiluminescent compound of formula (III):

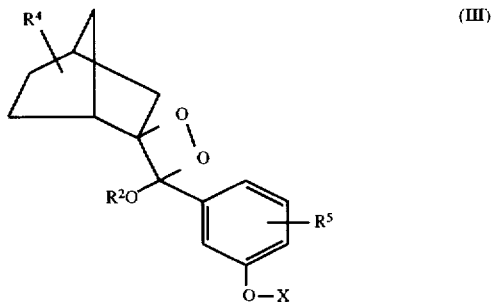

(III)

wherein $R^2$ is independently selected from the group consisting of $C_1$–$C_{10}$-alkyl, halo-$C_1$–$C_{10}$-alkyl, $C_1$–$C_{10}$-arylalkyl, carboxy-$C_1$–$C_{10}$-alkyl, hydroxy-$C_1$–$C_{10}$-alkyl, aldehydo-$C_1$–$C_{10}$-alkyl, amino-$C_1$–$C_{10}$-alkyl and thiol-$C_1$–$C_{10}$-alkyl;

$R^4$ is independently selected from the group consisting of hydrogen, $C_1$–$C_{10}$-alkyl, $C_1$–$C_{10}$-alkoxy, halo-$C_1$–$C_{10}$-alkyl and halogen;

$R^5$ is one to four groups independently selected from the group consisting of hydrogen, $C_1$–$C_{10}$-alkyl, $C_1$–$C_{10}$-alkoxy, $C_1$–$C_{10}$-alkylthio, halo-$C_1$–$C_{10}$-alkyl, $C_1$–$C_{10}$-alkylamino, $C_1$–$C_{10}$-dialkylamino and aryl-$C_1$–$C_{10}$-alkyl; and OX is a chemically labile group wherein the removal of X by an activating agent results in the formation of an aryl oxide intermediate; and (b) determining the reduction in binding of the indicator reagent by measuring the difference between the signals generated by the test sample and the control sample and correlating said reduction to the presence and/or amount of analyte in the sample.

2. The method of claim 1 wherein prior to step (a) the test sample is contacted with a solid phase to which the analyte-specific binding member has been attached.

3. The method of claim 2, wherein said solid phase is selected from the group consisting of magnetic beads, non-magnetic beads, wells of a reaction tray, microparticles, nylon strips and nitrocellulose strips.

4. The method of claim 1 wherein the signal generated is proportional to the amount of analyte in the test sample.

5. The method of claim 1 wherein said analyte-specific binding member is selected from the group consisting of an antigen, an antibody, a hapten, a polynucleotide, carbohydrate, and a small molecular weight analyte.

6. The method of claim 1, wherein R5 is at position 4 and is methyl or methoxy.

7. The method of claim 1, wherein bicyclo|2.2.1|heptyl when taken with $R^2$ is a compound of formula:

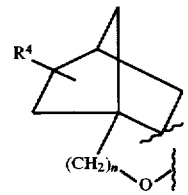

wherein $R^4$ is from zero to nine groups independently selected from the group consisting of hydrogen, $C_1$–$C_{10}$- alkyl, $C_1$–$C_{10}$-alkoxy, halo-$C_1$–$C_{10}$-alkyl, and halogen, and n is from one to three.

8. The method of claim 1 wherein in step (b) said signal represents more than 95% of the total light emitted by said indicator reagent within 0.1 to 0.5 seconds after the triggering of said indicator reagent with a trigger solution.

9. A competitive assay for determining the presence and/or amount of analyte in a test sample, comprising:

(a) contacting the test sample suspected of containing the analyte and a control sample free of the analyte with an analyte-specific binding member bound to a solid phase either before or during the assay and an enzyme conjugate comprising an enzyme and said analyte or derivative of said analyte and adding an indicator reagent capable of generating a measurable signal and comprising a compound of formula (III):

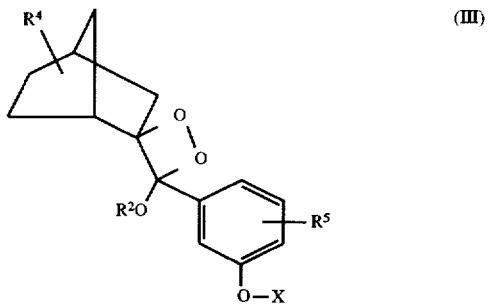

(III)

wherein $R^2$ is independently selected from the group consisting of $C_1$–$C_{10}$-alkyl, halo-$C_1$–$C_{10}$-alkyl, $C_1$–$C_{10}$-arylalkyl, carboxy-$C_1$–$C_{10}$-alkyl, hydroxy-$C_1$–$C_{10}$-alkyl, aldehydo-$C_1$–$C_{10}$-alkyl, amino-$C_1$–$C_{10}$-alkyl and thiol-$C_1$–$C_{10}$-alkyl;

$R^4$ is independently selected from the group consisting of hydrogen, $C_1$–$C_{10}$-alkyl, $C_1$–$C_{10}$-alkoxy, halo-$C_1$–$C_{10}$-alkyl and halogen;

$R^5$ is one to four groups independently selected from the group consisting of hydrogen, $C_1$–$C_{10}$-alkyl, $C_1$–$C_{10}$-alkoxy, $C_1$–$C_{10}$-alkylthio, halo-$C_1$–$C_{10}$-alkyl, $C_1$–$C_{10}$-alkylamino, $C_1$–$C_{10}$-dialkylamino and aryl-$C_1$–$C_{10}$-alkyl; and OX is a chemically labile group wherein the removal of X by an activating agent results in the formation of an aryl oxide intermediate; and for a time and under conditions sufficient to form indicator reagent/analyte-specific binding member-enzyme conjugate and/or analyte/analyte-specific binding member-enzyme conjugate complexes; and (b) determining the reduction in binding of the indicator reagent to the solid phase by measuring the difference between the signals generated by the test sample and the control sample and correlating said reduction to the presence and/or amount of analyte in the sample.

10. The method of claim 9, wherein said solid phase is selected from the group consisting of magnetic beads, non-magnetic beads, wells of a reaction tray, microparticles, nylon strips and nitrocellulose strips.

11. The method of claim 10 wherein the signal generated is proportional to the amount of analyte in the test sample.

12. The method of claim 9 wherein said analyte-specific binding member is selected from the group consisting of an antigen, an antibody, a hapten, a polynucleotide, carbohydrate, and a small molecular weight analyte.

13. The method of claim 9 wherein said enzyme is alkaline phosphatase or β-galactosidase.

14. The method of claim 9, wherein R5 is at position 4 and is methyl or methoxy.

15. The method of claim 9, wherein bicyclo[2.2.1]heptyl when taken with $R^2$ is a compound of formula:

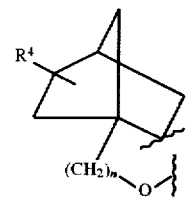

wherein $R^4$ is from zero to nine groups independently selected from the group consisting of hydrogen, $C_1$–$C_{10}$-alkyl, $C_1$–$C_{10}$-alkoxy, halo-$C_1$–$C_{10}$-alkyl, and halogen, and n is from one to three.

16. The method of claim 9 wherein in step (b) said signal represents more than 95% of the total light emitted by said indicator reagent within 0.1 to 0.5 seconds after the triggering of said indicator reagent with a trigger solution.

17. A competitive assay for determining the presence and amount of analyte in a test sample, comprising:

(a) contacting the test sample suspected of containing the analyte and a control sample free of the analyte with a solid phase to which an analyte-specific binding member has been attached and an indicator reagent capable of generating a measurable signal comprising (i) said analyte or analyte derivative and (ii) a compound of formula (III):

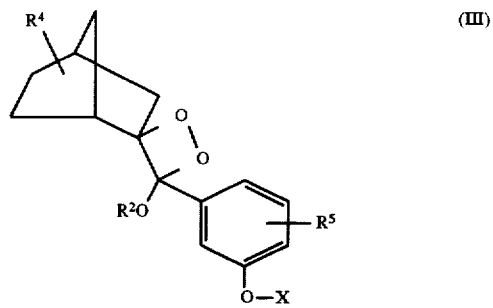

(III)

wherein $R^2$ is independently selected from the group consisting of $C_1$–$C_{10}$-alkyl, halo-$C_1$–$C_{10}$-alkyl, $C_1$–$C_{10}$-arylalkyl, carboxy-$C_1$–$C_{10}$-alkyl, hydroxy-$C_1$–$C_{10}$-alkyl, aldehydo-$C_1$–$C_{10}$-alkyl, amino-$C_1$–$C_{10}$-alkyl and thiol-$C_1$–$C_{10}$-alkyl;

$R^4$ is independently selected from the group consisting of $C_1$–$C_{10}$-alkyl, $C_1$–$C_{10}$-alkoxy, halo-$C_1$–$C_{10}$-alkyl and halogen;

$R^5$ is one to four groups independently selected from the group consisting of hydrogen, $C_1$–$C_{10}$-alkyl, $C_1$–$C_{10}$-alkoxy, $C_1$–$C_{10}$-alkylthio, halo-$C_1$–$C_{10}$-alkyl, $C_1$–$C_{10}$-alkylamino, $C_1$–$C_{10}$-dialkylamino and aryl-$C_1$–$C_{10}$-alkyl; and OX is a chemically labile group wherein the removal of X by an activating agent results in the formation of an aryl oxide intermediate; or a compound of formula (I):

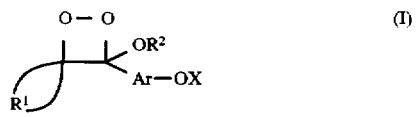

(I)

wherein Ar is an aryl group substituted with one to four groups independently selected from the group consisting of $C_1$–$C_{10}$-alkyl, $C_1$–$C_{10}$-alkoxy, $C_1$–$C_{10}$-alkylthio, halo-$C_1$–$C_{10}$-alkyl, $C_1$–$C_{10}$-alkylamino, di-($C_1$–$C_{10}$-alkyl)amino, aryl-$C_1$–$C_{10}$-alkyl, and halogen;

O—X is a chemically labile group wherein the removal of X by an activating agent results in the formation of an aryl oxide intermediate;

$R^1$ is a polycyclic alkylene of from 6 to 30 carbon atoms, optionally substituted with one to ten groups independently selected from $C_1$–$C_{10}$-alkyl, $C_1$–$C_{10}$-alkoxy, halogen and halo-$C_1$–$C_{10}$-alkyl; and $R^2$ is independently selected from the group consisting of $C_1$–$C_{10}$-alkyl, halo-$C_1$–$C_{10}$-alkyl, $C_1$–$C_{10}$-arylalkyl, carboxy-$C_1$–$C_{10}$-alkyl, hydroxy-$C_1$–$C_{10}$-alkyl, aldehydo-$C_1$–$C_{10}$-alkyl, amino-$C_1$–$C_{10}$-alkyl and thiol-$C_1$–$C_{10}$-alkyl;

for a time and under conditions sufficient to form a mixture of the test sample and solid phase and/or indicator reagent and solid phase;

(b) determining the reduction in binding of the indicator reagent to the solid phase by measuring the difference between the signals generated by the test sample and the control sample and correlating said reduction to the presence and/or amount of analyte in the sample.

18. The method of claim 17, wherein said solid phase is selected from the group consisting of magnetic beads, non-magnetic beads, wells of a reaction tray, microparticles, nylon strips and nitrocellulose strips.

19. The method of claim 17 wherein the signal generated is proportional to the amount of analyte in the test sample.

20. The method of claim 17 wherein said analyte-specific binding member is selected from the group consisting of an antigen, an antibody, a hapten, a polynucleotide, carbohydrate, and a small molecular weight analyte.

21. A competitive assay for determining the presence and/or amount of analyte in a test sample, comprising:

(a) contacting the test sample suspected of containing the analyte and a control sample free of the analyte with an analyte-specific binding-member bound to a solid phase either before or during the assay and an indicator reagent capable of generating a measurable signal comprising (i) said analyte or derivative of said analyte; and (ii) a chemiluminescent compound of formula (II):

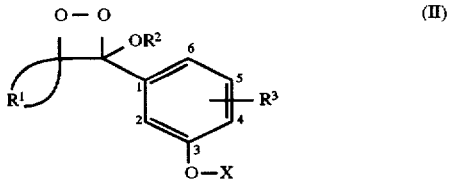

(II)

wherein $R^1$ is polycyclic alkylene of from 6 to 30 carbon atoms, optionally substituted with one to ten groups independently selected from $C_1$–$C_{10}$-alkyl, $C_1$–$C_{10}$-alkoxy, halogen and halo-$C_1$–$C_{10}$-alkyl;

$R^2$ is independently selected from the group consisting of $C_1$–$C_{10}$-alkyl, halo-$C_1$–$C_{10}$-alkyl, $C_1$–$C_{10}$-arylalkyl, carboxy-$C_1$–$C_{10}$-alkyl, hydroxy-C1–C10-alkyl, aldehydo-$C_1$–$C_{10}$-alkyl, amino-$C_1$–$C_{10}$-alkyl and thiol-$C_1$–$C_{10}$-alkyl;

$R^3$ is up to four groups selected from the group consisting of $C_1$–$C_{10}$-alkyl, $C_1$–$C_{10}$-alkoxy, $C_1$–$C_{10}$-alkylthio, halo-$C_1$–$C_{10}$-alkyl, $C_1$–$C_{10}$-alkylamino, di-($C_1$–$C_{10}$-alkyl)amino, aryl-$C_1$–$C_{10}$-alkyl and halogen, and O—X is a chemically labile group wherein the removal of X by an activating reagent results in the formation of an aryl oxide intermediate; and for a time and under conditions sufficient to form indicator reagent/analyte-specific binding member and/or analyte/analyte-specific binding member complexes; and (b) determining the reduction in binding of the indicator reagent to the solid phase by measuring the difference between the signals generated by the test sample and the control sample and correlating said reduction to the presence and/or amount of analyte in the sample.

22. The method of claim 21, wherein R1 is substituted or unsubstituted adamantyl or bicyclo|2.2.1| heptyl, and R3 is at position 4 and is C1–C10 alkyl or C1–C10 alkoxy.

23. The method of claim 22, wherein R3 is methyl or methoxy.

24. The method of claim 22 wherein the compound defined by formula (II) is selected from the group consisting of 4-(3-tert-butyldimethylsilyloxy-4-methoxyphenyl)-4-methoxyspiro|1,2-dioxetane-3,2'-adamantane|; 4-(3-phosphate-4-methoxyphenyl)-4-methoxyspiro|1,2-dioxetane-3,2'-adamantane|, tetra-ethylammonium salt; and 4-(3-tert-butyldimethylsilyloxy-4-methoxyphenyl)-4-(hydroxy)butyloxyspiro|1,2-dioxetane-3,2'adamantane|.

25. The method of claim 23 wherein the compound defined by formula (II) is selected from the group consisting of 4-(3-tert-butyldimethylsilyloxy-4-methylphenyl)-4-methoxyspiro|1,2-dioxetane-3,2'-(1',7',7'-trimethyl bicyclo |2.2.1|heptane); 4-(3-tert-butyldimethylsilyloxy-4-methoxyphenyl)-4-methoxyspiro (1,2-dioxetane-3,2'-1',7',7'-trimethylbicyclo|2.2.1|heptane); 4-(3-tert-butyldimethylsilyloxy-4-methoxyphenyl)-4-(4-hydroxybutyloxy)spiro (1,2-dioxetane-3,2'-(1',7',7'-trimethylbicyclo|2.2.1|heptane); and 4-(3-tert-butyldimethylsilyloxy-4-methoxy)phenylspiro)-(4,1'-(epoxymethano)-1,2-dioxetane-3,2'-(7',7'-dimethylbicyclo|2.2.1|heptane).

26. A competitive assay for determining the presence and/or amount of analyte in a test sample, comprising:

(a) contacting the test sample suspected of containing the analyte and a control sample free of the analyte with an analyte-specific binding member bound to a solid phase either before or during the assay, and an indicator reagent capable of generating a measurable signal comprising (i) said analyte or derivative of said analyte; and (ii) a chemiluminescent compound of formula (I)

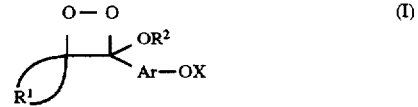

(I)

wherein Ar is an aryl group with one to four groups independently selected from the group consisting of $C_1$–$C_{10}$-alkyl, $C_1$–$C_{10}$-alkoxy, $C_1$–$C_{10}$-alkylthio, halo-$C_1$–$C_{10}$-alkyl, C1–$C_{10}$-alkylamino, di-($C_1$–$C_{10}$-alkyl)amino, aryl-$C_1$–$C_{10}$-alkyl, and halogen;

O—X is a chemically labile group wherein the removal of X by an activating agent results in the formation of an aryl oxide intermediate;

$R^1$ is independently selected from the group consisting of bicyclo|2.2.1|heptyl and adamantyl optionally substituted with one to ten groups independently selected from $C_1$–$C_{10}$-alkyl, $C_1$–$C_{10}$-alkoxy, halogen and halo-$C_1$–$C_{10}$-alkyl and $R^2$ is independently selected from the group consisting of $C_1$–$C_{10}$-alkyl, halo-$C_1$–$C_{10}$-alkyl, $C_1$–$C_{10}$-arylalky, carboxy-$C_1$–$C_{10}$-alkyl, amino-$C_1$–$C_{10}$-alkyl and thiol-$C_1$–$C_{10}$-alkyl; or $R^1$ when taken with $R^2$ is a compound of formula;

37

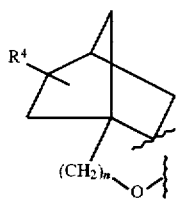

wherein $R^4$ is from zero to nine groups independently selected from the group consisting of hydrogen, $C_1-C_{10}$-alkyl, $C_1-C_{10}$-alkoxy, halo-$C_1-C_{10}$-alkyl, and halogen, and n is from one to three for a time and under conditions sufficient to from indicator reagent/analyte-specific binding member and/or analyte/analyte-specific binding member complexes; and (b) determining the reduction in binding of the indicator reagent to the solid phase by measuring the difference between the signals generated by the test sample and the control sample and correlating said reduction to the presence and/or amount of analyte in the sample.

27. A competitive assay for determining the presence and/or amount of analyte in a test sample, comprising (a) contacting the test sample suspected of containing the analyte and a control sample free of the analyte with an analyte-specific binding member and an enzyme conjugate comprising an enzyme and said analyte or derivative of said analyte and adding an indicator reagent capable of generating a measurable signal and which comprises a compound of the formula (II):

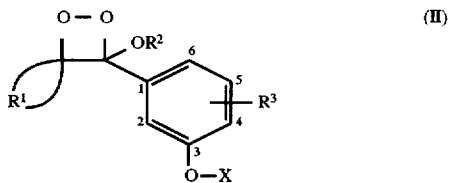

(II)

wherein $R^1$ is a polycyclic alkylene of from 6 to 30 carbon atoms, optionally substituted with one to ten groups independently selected from $C_1-C_{10}$-alkyl, $C_1-C_{10}$-alkoxy, halogen and halo-$C_1-C_{10}$-alkyl;

$R^2$ is independently selected from the group consisting of $C_1-C_{10}$-alkyl, halo-$C_1-C_{10}$-alkyl, $C_1-C_{10}$-arylalkyl, carboxy-$C_1-C_{10}$-alkyl, hydroxy-C1–C10-alkyl, aldehydo-$C_1-C_{10}$-alkyl, amino-$C_1-C_{10}$-alkyl and thiol-$C_1-C_{10}$-alkyl;

R3 is up to four groups selected from the group consisting of $C_1-C_{10}$-alkyl, $C_1-C_{10}$-alkoxy, $C_1-C_{10}$-alkylthio, halo-$C_1-C_{10}$-alkyl, $C_1-C_{10}$-alkylamino, di-($C_1-C_{10}$-alkyl) amino, aryl-$C_1-C_1$-alkyl and halogen, and O—X is a chemically labile group wherein the removal of X by an activating reagent results in the formation of an aryl oxide, intermediate; and for a time and under conditions sufficient to form indicator reagent/analyte-specific binding member and/or analyte/analyte-specific binding member complexes; and (b) determining the reduction in binding of the indicator reagent by measuring the difference between the signals generated by the test sample and the control sample and correlating said reduction to the presence and/or amount of analyte in the sample.

28. The method of claim 27, wherein R1 is substituted or unsubstituted adamantyl or bicyclo|2.2.1| heptyl, and R3 is at position 4 and is C1–C10 alkyl or C1–C10 alkoxy.

29. The method of claim 28, wherein R3 is methyl or methoxy.

30. The method of claim 28 wherein the compound defined by formula (II) is selected from the group consisting of 4-(3-tert-butyldimethylsilyloxy-4-methoxyphenyl)-4-methoxyspiro|1,2-dioxetane-3,2'-adamantane|; 4-(3-phosphate-4-methoxyphenyl)-4-methoxyspiro|1,2-dioxetane-3,2'-adamantane|, tetra-ethylammonium salt; and 4-(3-tert-butyldimethylsilyloxy-4-methoxyphenyl)-4-(hydroxy)butyloxyspiro|1,2-dioxetane-3,2'adamantane|.

31. The method of claim 29 wherein the compound defined by formula (II) is selected from the group consisting of 4-(3-tert-butyldimethylsilyloxy-4-methylphenyl)-4-methoxyspiro|1,2-dioxetane-3,2'-(1',7',7'-trimethyl bicyclo |2.2.1|heptane); 4-(3-tert-butyldimethylsilyloxy-4-methoxyphenyl)-4-methoxyspiro (1,2-dioxetane-3,2'-1',7', 7'-trimethylbicyclo|2.2.1|heptane); 4-(3-tert-butyldimethylsilyloxy-4-methoxyphenyl)-4-(4-hydroxybutyloxy)spiro (1,2-dioxetane-3,2'-(1',7',7'-trimethylbicyclo|2.2.1|heptane); and 4-(3-tert-butyldimethylsilyloxy-4-methoxy)phenylspiro)-(4,1'-(epoxymethano)-1,2-dioxetane-3,2'-:(7',7'-dimethylbicyclo |2.2.1|heptane).

32. A competitive assay for determining the presence and/or amount of analyte in a test sample, comprising;

(a) contacting the test sample suspected of containing the analyte and a control sample free of the analyte with an analyte-specific binding member and an enzyme conjugate comprising an enzyme and said analyte or derivative of said analyte and adding an indicator reagent capable of generating a measurable signal and which comprises a compound of formula (I)

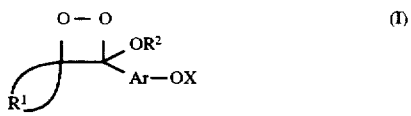

(I)

wherein Ar is an aryl group with one to four groups independently selected from the group consisting of $C_1-C_{10}$-alkyl, $C_1-C_{10}$-alkoxy, $C_1-C_{10}$-alkylthio, halo-$C_1-C_{10}$-alkyl, C1–$C_{10}$-alkylamino, di-($C_1-C_{10}$-alkyl) amino, aryl-$C_1-C_{10}$-alkyl, and halogen;

O—X is a chemically labile group wherein the removal of X by an activating agent results in the formation of an aryl oxide intermediate;

$R^1$ is independently selected from the group consisting of bicyclo|2.2.1|heptyl and adamantyl optionally substituted with one to ten groups independently selected from $C_1-C_{10}$-alkyl, $C_1-C_{10}$-alkoxy, halogen and halo-$C_1-C_{10}$-alkyl and $R^2$ is independently selected from the group consisting of $C_1-C_{10}$-alkyl, halo-$C_1-C_{10}$-alkyl, $C_1-C_{10}$-arylalky, carboxy-$C_1-C_{10}$-alkyl, amino-$C_1-C_{10}$-alkyl and thiol-$C_1-C_{10}$-alkyl; or $R^1$ when taken with $R^2$ is a compound of formula:

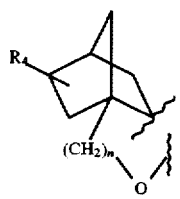

wherein $R^4$ is from zero to nine groups independently selected from the group consisting of hydrogen, $C_1$–$C_{10}$-alkyl, $C_1$–$C_{10}$-alkoxy, halo-$C_1$–$C_{10}$-alkyl, and halogen, and n is from one to three for a time, and under conditions sufficient to from indicator reagent/analyte-specific binding member and/or analyte/analyte-specific binding member complexes; and (b) determining the reduction in binding of the indicator reagent by measuring the difference between the signals generated by the test sample and the control sample and correlating said reduction to the presence and/or amount of analyte in the sample.

* * * * *

UNITED STATES PATENT AND TRADEMARK OFFICE
CERTIFICATE OF CORRECTION

PATENT NO. : 5,780,249
DATED : July 14, 1998
INVENTOR(S) : Wang et al.

It is certified that error appears in the above-indentified patent and that said Letters Patent is hereby corrected as shown below:

Column 36, line 53, change "Cl" to -- $C_1$ --.

Column 37, line 55, change "oxide," to --oxide--.

Column 38, line 15, change "trimethyl bicyclo" to --trimethylbicyclo--.

Column 38, line 43, change "Cl" to -- $C_1$ --.

Signed and Sealed this

Twenty-sixth Day of October, 1999

Attest:

Q. TODD DICKINSON

*Attesting Officer*  *Acting Commissioner of Patents and Trademarks*